(12) United States Patent
Okiyama

(10) Patent No.: US 12,245,754 B2
(45) Date of Patent: Mar. 11, 2025

(54) PHARMACEUTICAL COMPOSITION FOR TREATING INFLUENZA VIRUS INFECTIONS

(71) Applicant: AILLIS INC., Tokyo (JP)

(72) Inventor: Syou Okiyama, Tokyo (JP)

(73) Assignee: AILLIS INC. (JP)

( * ) Notice: Subject to any disclaimer, the term of this patent is extended or adjusted under 35 U.S.C. 154(b) by 432 days.

(21) Appl. No.: 17/623,376

(22) PCT Filed: Jun. 30, 2020

(86) PCT No.: PCT/JP2020/025652
§ 371 (c)(1),
(2) Date: Dec. 28, 2021

(87) PCT Pub. No.: WO2021/002355
PCT Pub. Date: Jan. 7, 2021

(65) Prior Publication Data
US 2022/0361741 A1    Nov. 17, 2022

(30) Foreign Application Priority Data
Jul. 3, 2019    (JP) .................................. 2019-124750

(51) Int. Cl.
*A61B 1/24*    (2006.01)
*A61K 31/196*    (2006.01)
(Continued)

(52) U.S. Cl.
CPC .............. *A61B 1/24* (2013.01); *A61K 31/196* (2013.01); *A61K 31/215* (2013.01);
(Continued)

(58) Field of Classification Search
CPC ..... A61B 1/24; A61B 5/4866; A61B 5/14532; A61B 5/0077; A61B 5/0088;
(Continued)

(56) References Cited

U.S. PATENT DOCUMENTS

2021/0059534 A1*    3/2021    Okiyama ............... A61B 5/742

FOREIGN PATENT DOCUMENTS

| CN | 109504721 A | 3/2019 |
| JP | 2018-120430 A | 8/2018 |

(Continued)

OTHER PUBLICATIONS

Tsuneaki Kenzaka, Influenza follicles in the posterior pharyngeal wall, Postgraduate Medical Journal, vol. 91, Issue 1078, Aug. 2015, p. 472 (Year: 2015).*

(Continued)

*Primary Examiner* — Neil R McLean
(74) *Attorney, Agent, or Firm* — Harness, Dickey & Pierce, P.L.C.

(57) ABSTRACT

A pharmaceutical composition for treating an influenza virus infectious disease, containing an anti-influenza virus agent as an active ingredient is provided. The anti-influenza virus agent is administered to a patient determined to be positive for the influenza virus infectious disease based on an intraoral image captured using an intraoral imaging apparatus.

18 Claims, 18 Drawing Sheets

(51) Int. Cl.
    *A61K 31/215*     (2006.01)
    *A61K 31/351*     (2006.01)
    *A61K 31/5383*     (2006.01)
    *G06T 7/00*     (2017.01)

(52) U.S. Cl.
    CPC ........ *A61K 31/351* (2013.01); *A61K 31/5383* (2013.01); *G06T 7/0012* (2013.01)

(58) Field of Classification Search
    CPC ....... A61B 5/02028; A61B 5/08; A61B 5/201; A61B 5/4848; A61B 5/682; A61K 31/196; A61K 31/215; A61K 31/351; A61K 31/5383; A61K 31/7012; A61K 45/00; G06T 7/0012; A61P 31/16; G16B 50/20
    USPC .......................................................... 382/128
    See application file for complete search history.

(56) References Cited

FOREIGN PATENT DOCUMENTS

| WO | 2016-185463 | A1 | 11/2016 |
|---|---|---|---|
| WO | 2019-131327 | A1 | 7/2019 |

OTHER PUBLICATIONS

Tsuneaki Kenzaka "Influenza follicles in the posterior pharyngeal wall"; Postgraduate Medical Journal; vol. 91, No. 1078; p. 472; Aug. 1, 2015 (total 1 page).

Miyamoto A. et al. "Influenza follicles and their buds as early diagnostic markers of influenza: typical images"; Postgraduate Medical Journal; vol. 92, No. 1091; pp. 560-561; Sep. 1, 2016 (total 2 pages).

Kamali et al. "Influenza treateement and prophylaxis with neuraminidase inhibitors: a review"; Infection and Drug Resistance; vol. 6; pp. 187-198; Nov. 1, 2013 (total 12 pages).

Robert Welliver et al. "Efectiveness of Oseltamivir in Preventing Influenza in Household Contacs—A Randomized Controlled Trial"; Jama the Journal of the American Medical Association; vol. 285, No. 6; pp. 748-754; Feb. 14, 2001 (total 7 pages).

Arnold S. Monto et al. "Zanamivir Prophylaxis: An Effective Strategy for the Prevention of Influenza Types A and B within Households"; Journal of Infectious Diseases; vol. 186; pp. 1582-1588; Dec. 1, 2002 (total 7 pages).

European Seach Report issued in the corresponding European Patent Application No. 20834184.2; dated Jun. 19, 2023 (total 12 pages).

Masafumi Seki "Special issue: Latest information on influenza treatment, Guidelines for using anti-influenza drugs, IV Preventive administration, etc"; The Japanese Journal of Clinical and Experimental Medicine; Year 2018; vol. 95, No. 11; pp. 16-18, particularly p. 16, Table 1 & p. 18 (total 4 pages); English abstract only.

Naoki Kawai et al. "Special issue: Latest information on influenza treatment, Preventive measures against and response at the time of outbreak to influenza epidemic at home"; The Japanese Journal of Clinical and Experimental Medicine; Year 2018; vol. 95, No. 11; pp. 54-59, particularly introduction, right column of p. 55, right column of p. 56, pp. 57-58 V, Fig. 3, Second paragraph of the right column on p. 56 (total 7 pages); English abstract only.

Article from Nikkei Business Daily newspaper dated Jun. 29, 2019; "AI Influenza Diagnostics by Aillis—Quick and accurate based on throat image (Transform your health care with this)"; p. 12 (total 3 pages); summarized in English.

Akihiko Miyamoto, MD, PhD et al. "Poster Pharyngeal Wall Follicles as Early Diagnostic Marker for Seasonal and Novel Influenza"; Diagnosis of Seasonal and Novel Influenza from Pharyngeal Follicles; Year 2011; vol. 12; pp. 51-60 (total 10 pages).

Article from Weekly Toyo Keizai dated Apr. 20, 2019; "Digital Revolution in Medical Field—AI doctor is coming true" Special Issue 1—Boiling! Advanced Medical Venture; pp. 36-39 (total 8 pages).

Akihiko Miyamoto et al. "Posterior Pharyngeal Wall Follicles as a Diagnostic Marker of Influenza During Physical Examination: Considering Their Meaning and Value"; Nichidai Medical Journal; Year 2013; vol. 72 (1); pp. 11-18 (total 8 pages); English abstract only.

Office Action issued in the corresponding Chinese Patent Application No. 2020800614219; issued on Apr. 26, 2024 (total 21 pages).

\* cited by examiner

PHARMACEUTICAL COMPOSITION FOR TREATING INFLUENZA VIRUS INFECTIONS

CROSS REFERENCE TO RELATED APPLICATIONS

This application is a U.S. National Phase application under 35 U.S.C. 371 of International Application No. PCT/JP2020/025652, filed on Jun. 30, 2020, which claims priority to Japanese Patent Application No. 2019-124750, filed on Jul. 3, 2019. The entire disclosures of the above applications are expressly incorporated by reference herein.

BACKGROUND

Technical Field

The present invention relates to a pharmaceutical composition for treating an influenza virus infectious disease. Alternatively, it may be said that the present invention relates to a treatment method and prevention method for an influenza virus infectious disease, containing an anti-influenza virus agent as an active ingredient, and to a use of an active ingredient for manufacturing an anti-influenza virus agent for treating and preventing an influenza virus infectious disease.

Background Art

In Miyamoto and Watanabe, "Posterior Pharyngeal Wall Follicles as a Diagnostic Marker of Influenza During Physical Examination: Considering Their Meaning and Value", Journal of Nihon University Medical Association 72(1): 11-18, there is a report that lymph follicles appearing at the deepest part of the pharynx have a pattern peculiar to an influenza virus infectious disease. The lymph follicles having such pattern are referred to as "influenza follicles". The influenza follicles are a characteristic sign of influenza, and are considered to appear about 2 hours after the onset.

Accurate discrimination of influenza follicles is expected to lead to a dramatic improvement in diagnostic accuracy. However, appropriate decision of influenza follicles requires intensive training through a large number of cases and is never easy for general physicians. Unfortunately, the findings of the above-mentioned studies have been only utilized among a limited number of physicians. For this reason, there is room for improvement in efficiency in treating an influenza virus infectious disease.

In view of the foregoing, an object of the present invention is to improve the efficiency in treating an influenza virus infectious disease.

SUMMARY

In order to achieve the above-mentioned object, according to a first embodiment of the present invention, there is provided a pharmaceutical composition for treating an influenza virus infectious disease, including an anti-influenza virus agent as an active ingredient, wherein the anti-influenza virus agent is administered to a patient determined to be positive for the influenza virus infectious disease based on an intraoral image captured using an intraoral imaging apparatus.

In the pharmaceutical composition for treating an influenza virus infectious disease according to the first embodiment of the present invention having the above-mentioned configuration, the intraoral imaging apparatus may include: an imaging device configured to acquire an image of an inside of a mouth; a light source configured to emit light to a subject of the imaging device; a storage device configured to store an algorithm for determining presence or absence of an influenza virus infectious disease; and an arithmetic unit, and the arithmetic unit may be configured to execute: determination processing for determining a possibility of the influenza virus infectious disease based on the image and the algorithm; and output processing for outputting a result of the determination processing.

In addition, in the pharmaceutical composition for treating an influenza virus infectious disease according to the first embodiment of the present invention having the above-mentioned configuration, the imaging device may be configured to acquire an image of a pharynx, and the determination processing may include determination of whether a pattern peculiar to the influenza virus infectious disease appears in the pharynx.

In addition, in the pharmaceutical composition for treating an influenza virus infectious disease according to the first embodiment of the present invention having the above-mentioned configuration, the anti-influenza virus agent may be selected from the group consisting of: baloxavir; oseltamivir; zanamivir; peramivir; and laninamivir, but is not limited thereto.

In addition, according to a second embodiment of the present invention, there is provided a pharmaceutical composition for preventing an influenza virus infectious disease, including an anti-influenza virus agent as an active ingredient, wherein the anti-influenza virus agent is administered to a close contact of a patient determined to be positive for the influenza virus infectious disease based on an intraoral image captured using an intraoral imaging apparatus. The term "close contact" as used herein refers to, for example, a person who has acted with a patient determined to be suspected of the influenza virus infectious disease, has touched the patient, or has sat in a seat near the patient in an aircraft, a workplace, or the like, and the term encompasses family members living together and people living together.

In addition, in the pharmaceutical composition for preventing an influenza virus infectious disease according to the second embodiment of the present invention having the above-mentioned configuration, the close contact may be an elderly person aged 65 or more, a patient with a chronic respiratory disease or a chronic heart disease, a patient with a metabolic disease including diabetes, or a patient with renal dysfunction, who may become a high-risk patient when infected with the influenza virus infectious disease.

In addition, in the pharmaceutical composition for preventing an influenza virus infectious disease according to the second embodiment of the present invention having the above-mentioned configuration, the intraoral imaging apparatus may include: an imaging device configured to acquire an image of an inside of a mouth; a light source configured to emit light to a subject of the imaging device; a storage device configured to store an algorithm for determining presence or absence of an influenza virus infectious disease; and an arithmetic unit, and the arithmetic unit may be configured to execute: determination processing for determining a possibility of the influenza virus infectious disease based on the image and the algorithm; and output processing for outputting a result of the determination processing.

In addition, in the pharmaceutical composition for preventing an influenza virus infectious disease according to the second embodiment of the present invention having the above-mentioned configuration, the imaging device may be configured to acquire an image of a pharynx, and the determination processing may include determination of whether a pattern peculiar to the influenza virus infectious disease appears in the pharynx.

In addition, according to a third embodiment of the present invention, there is provided a pharmaceutical composition for preventing an influenza virus infectious disease, including an anti-influenza virus agent as an active ingredient, wherein the anti-influenza virus agent is administered to a person determined to be negative for the influenza virus infectious disease based on an intraoral image captured using an intraoral imaging apparatus, a close contact of the person including a patient who has developed the influenza virus infectious disease.

In the pharmaceutical composition for preventing an influenza virus infectious disease according to the third embodiment of the present invention having the above-mentioned configuration, the person may be an elderly person aged 65 or more, a patient with a chronic respiratory disease or a chronic heart disease, a patient with a metabolic disease including diabetes, or a patient with renal dysfunction.

In the pharmaceutical composition for preventing an influenza virus infectious disease according to the third embodiment of the present invention having the above-mentioned configuration, the intraoral imaging apparatus may include: an imaging device configured to acquire an image of an inside of a mouth; a light source configured to emit light to a subject of the imaging device; a storage device configured to store an algorithm for determining presence or absence of an influenza virus infectious disease; and an arithmetic unit, and the arithmetic unit may be configured to execute: determination processing for determining a possibility of the influenza virus infectious disease based on the image and the algorithm; and output processing for outputting a result of the determination processing.

In the pharmaceutical composition for preventing an influenza virus infectious disease according to the third embodiment of the present invention having the above-mentioned configuration, the imaging device may be configured to acquire an image of a pharynx, and the determination processing may include determination of whether a pattern peculiar to the influenza virus infectious disease appears in the pharynx.

Advantageous Effects of Invention

According to the present invention, it is possible to improve the efficiency in treating an influenza virus infectious disease.

DETAILED DESCRIPTION

Now, a typical embodiment of the present invention is described in detail with reference to the accompanying drawings. However, the present invention is not limited to the embodiment and the drawings. Further, the drawings are provided in order to conceptually illustrate the present invention, and hence dimensions, ratios, or numbers may be exaggerated or simplified as required for easy understanding. In addition, in the following disclosure, an influenza virus infectious disease may be abbreviated as "influenza." Further, the range "from X to Y" referred to in this specification means "X or more and Y or less."

In this embodiment, it is assumed that a medical apparatus including an intraoral imaging apparatus is used for determining presence or absence of influenza, and that an anti-influenza virus agent is administered to a patient determined to be positive for an influenza virus infectious disease and family members living together the patient or people living together the patient. In this case, it is assumed that an intraoral imaging assistance tool is used to capture an image of the inside of a mouth (in particular, pharynx), but the present invention is not limited thereto. In addition, the intraoral imaging assistance tool may also be used in combination with other devices, for example, a smartphone and a tablet terminal.

Now, the intraoral imaging assistance tool and the intraoral imaging apparatus which are included in the medical apparatus are described, and then a procedure up to the administration of the anti-influenza virus agent is described.

1 Outline of Medical Apparatus

Figure 1:
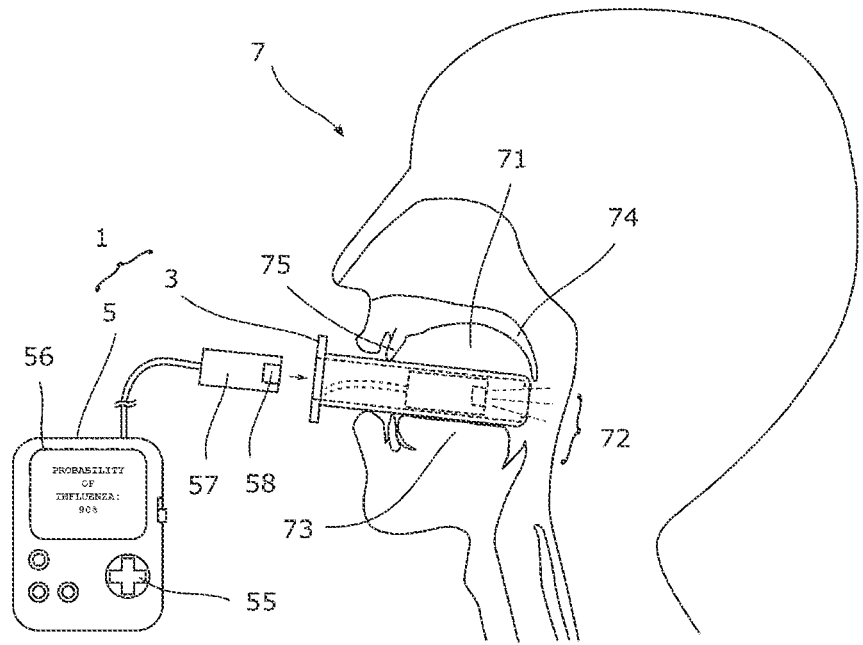
FIG. 1 is a schematic view of a medical apparatus (1) including an intraoral imaging apparatus (5) and an intraoral imaging assistance tool (3) in a typical embodiment of the present invention.

An outline of a medical apparatus 1 in this embodiment is described with reference to FIG. 1. As illustrated in FIG. 1, the medical apparatus 1 includes an intraoral imaging apparatus 5 and an intraoral imaging assistance tool 3. It is preferred that the intraoral imaging apparatus 5 be used in combination with the intraoral imaging assistance tool 3, but may be used alone or in combination with another assistance tool.

The intraoral imaging apparatus 5 includes an imaging device 57 for acquiring an image of a subject, and dedicated software is installed in advance in this apparatus 5. A user (for example, doctor) causes a determination target person (for example, patient) suspected of having influenza to hold the intraoral imaging assistance tool 3 in his or her mouth, to thereby secure a field of view for imaging. After that, the user inserts the imaging device 57 into the intraoral imaging assistance tool 3 and captures an image of a pharynx 72 of that target person 7. The user can also capture an image of an intraoral cavity 71 of the target person 7 by adjusting an insertion depth and insertion angle of the intraoral imaging assistance tool 3. In another case, the user may insert the intraoral imaging assistance tool 3 having the imaging device 57 received therein into the inside of the mouth of the determination target person 7, or may have the determination target person 7 insert the intraoral imaging assistance tool 3 into the inside of the mouth.

The captured image is processed in accordance with a previously generated determination algorithm. The processing is assumed to be performed by the intraoral imaging apparatus 5, but the processing may be performed by another computer. For example, the determination algorithm detects influenza follicles or another pharyngeal symptom (pattern) peculiar to influenza, and displays a probability of influenza. Thus, for example, even an inexperienced doctor or an intern can perform an accurate and early diagnosis of influenza. Meanwhile, even an experienced doctor can obtain useful judgment materials. In addition, an increase in rate of correct influenza diagnosis enables the patient to complete an outpatient treatment with a single consultation, and also provides the patient with an appropriate treatment from an earlier stage.

2-1 Intraoral Imaging Assistance Tool

Figure 2:
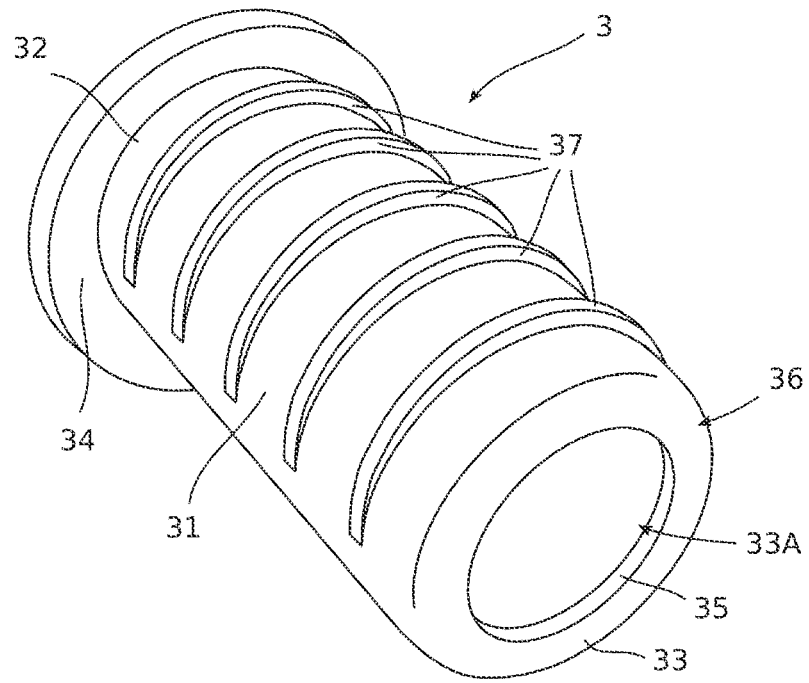
FIG. 2 is a perspective view for illustrating the intraoral imaging assistance tool (3) of FIG. 1.
Figure 3:
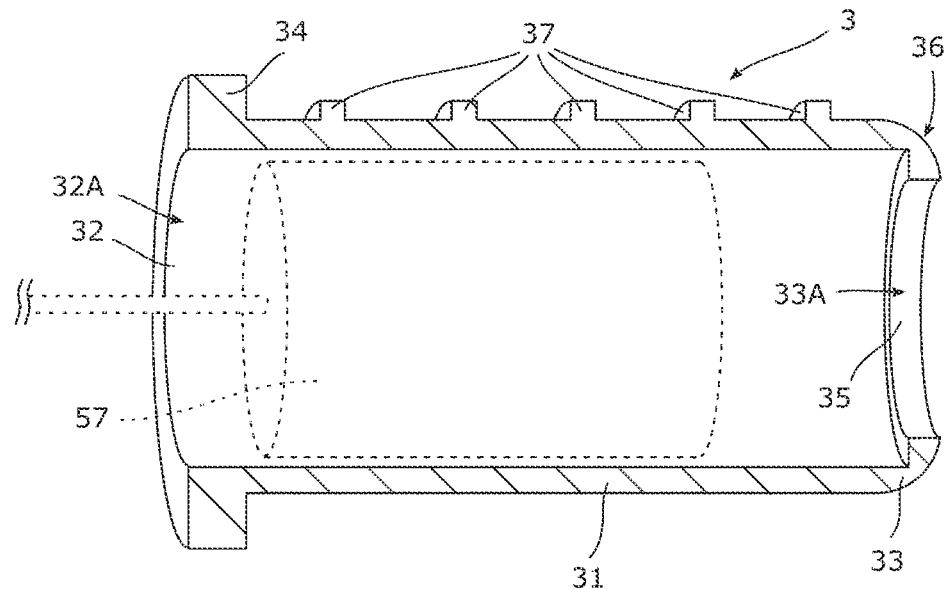
FIG. 3 is a longitudinal sectional view for illustrating the intraoral imaging assistance tool (3) of FIG. 2.
Figure 4:
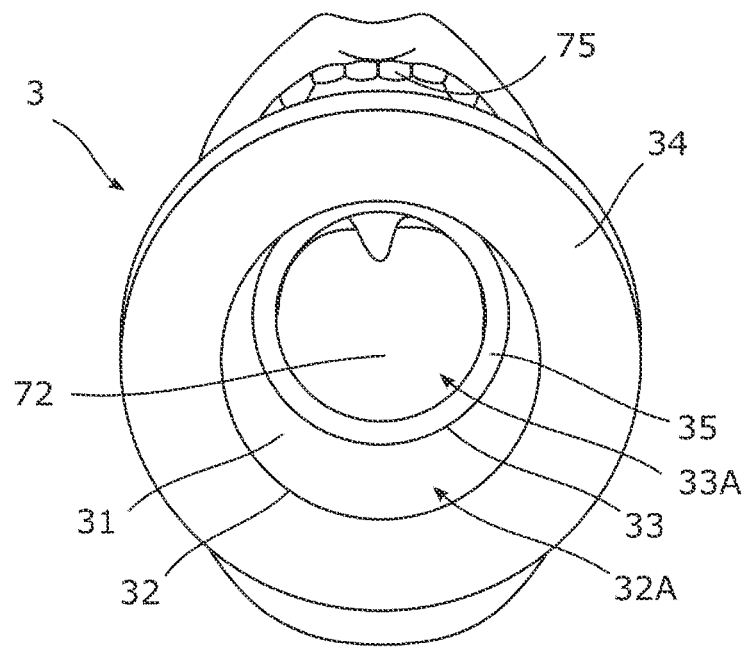
FIG. 4 is a view for illustrating an example of a state in which the intraoral imaging assistance tool (3) of FIG. 2 is inserted into an intraoral cavity (71).

Referring to FIG. 2 to FIG. 4, the intraoral imaging assistance tool 3 in this embodiment is described in detail.

The intraoral imaging assistance tool 3 is an auxiliary tool to be used for imaging the inside of the mouth (intraoral cavity 71 and pharynx 72) of the person (determination target person) 7. More specifically, the intraoral imaging assistance tool 3 is used for obtaining a satisfactory field of view of an imaging region including the intraoral cavity 71 or the pharynx 72 by being inserted into the intraoral cavity 71 at a time of intraoral imaging. From the viewpoint of obtaining a more satisfactory field of view, it is preferred that the intraoral imaging assistance tool 3 have translucency. In this embodiment, a mouthpiece is assumed as an example of the intraoral imaging assistance tool 3, but the present invention is not limited thereto.

As illustrated in FIG. 2, the intraoral imaging assistance tool 3 includes a main body 31, a flange portion 34, and a regulating portion 35. However, it is sufficient for the intraoral imaging assistance tool 3 to include the main body 31, and the intraoral imaging assistance tool 3 is not required to include both or one of the flange portion 34 and the regulating portion 35. In this embodiment, an integrally molded resin product is assumed as the intraoral imaging assistance tool 3, but the intraoral imaging assistance tool 3 may be made of another material, for example, paper, cloth, elastic rubber, or metal, or may be made of a plurality of materials. The intraoral imaging assistance tool 3 is also assumed to be a tool of a disposable type, but may be a tool of a reusable type.

Figure 27:
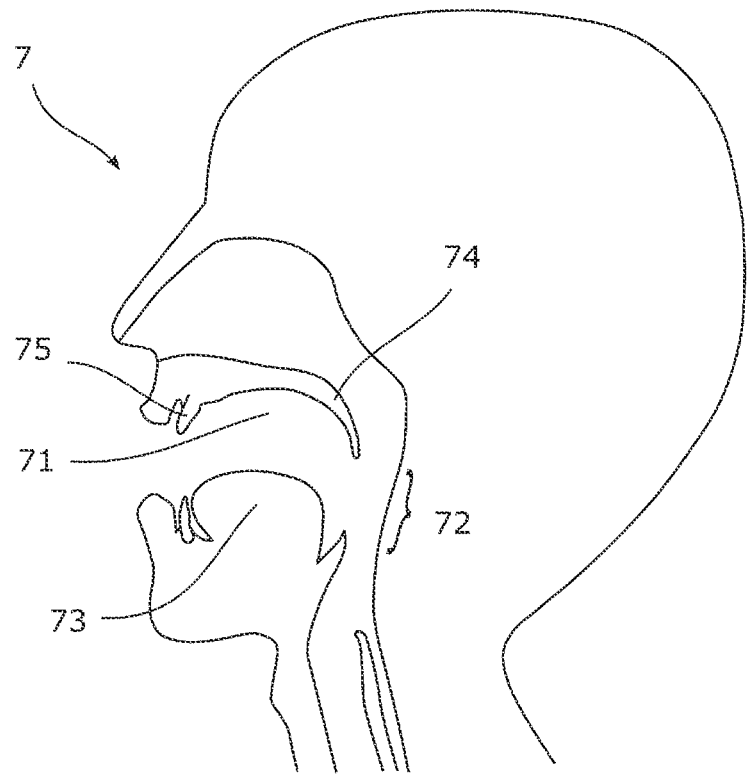
FIG. 27 is a schematic view of a cross-sectional shape of a head of a person (7).
Figure 28:
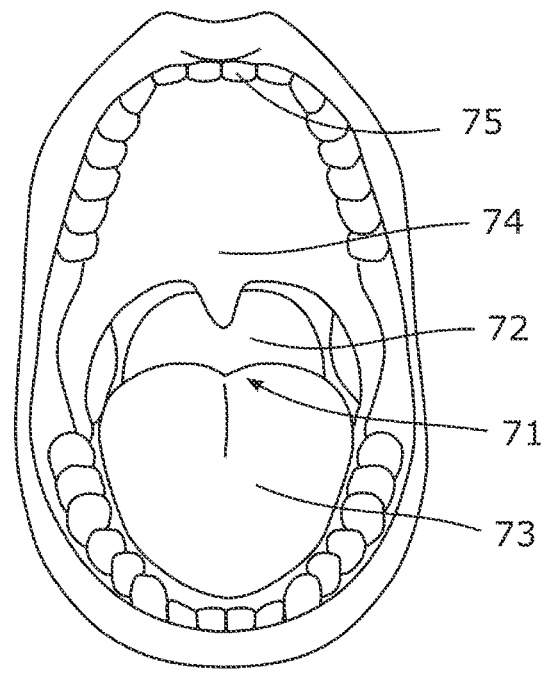
FIG. 28 is a schematic view of the intraoral cavity (71).

The main body 31 exhibits a cylindrical shape as a whole. When the main body 31 is deeply inserted into the intraoral cavity 71, a tongue 73 is pushed downward and a soft palate 74 is pushed upward as can be understood from a comparison between, for example, FIG. 1 and FIG. 27. In short, the intraoral imaging assistance tool 3 can be said to be a tongue depressor. Thus, as can be understood from a comparison between, for example, FIG. 4 and FIG. 28, a satisfactory field of view of the pharynx 72 can be secured from the inside of the intraoral imaging assistance tool 3 (main body 31).

In this embodiment, the main body 31 extends substantially linearly. That is, an inner diameter and outer diameter of the main body 31 are substantially constant over a longitudinal direction thereof. However, as long as the main body 31 does not interfere with sliding of the imaging device 57 on an inner peripheral surface of the main body 31, the main body 31 may be partially or wholly curved, or the inner diameter or outer diameter of the main body 31 may be changed.

A cross-sectional shape of the main body 31 is assumed to have a perfect circle here. However, the cross-sectional shape may be an elliptical shape, may be a quadrangle or another polygonal cross-section, or may be an asymmetrical shape, for example, a substantially D-shape. When the main body 31 has an elliptical shape, a polygonal shape, or an asymmetrical cross-sectional shape, movement (that is, rotation) of the imaging device 57 corresponding to the shape of the main body 31 in a circumferential direction of the main body 31 centered on an axial direction of the main body 31 is regulated or suppressed at a time of the sliding in the main body 31, and hence it is possible to obtain intraoral images having orientations aligned, which are suitable for determination.

When the main body 31 has a perfect circular cross-sectional shape, as described later with reference to FIG. 6, rails and protruding portions which engage with each other may be provided on an outer surface of the imaging device 57 and the inner peripheral surface of the main body 31, to thereby regulate the rotation of the imaging device 57 in the main body 31.

As illustrated in FIG. 3, the main body 31 includes end portions 32 and 33 positioned on opposite sides of each other. When the intraoral imaging assistance tool 3 is attached to the intraoral cavity 71, the end portion 32 is exposed to the outside, and the end portion 33 is positioned in the intraoral cavity 71.

The outer peripheral surface of the main body 31 is smooth, and the main body 31 and the end portion 33 are also integrally connected to each other in a smoothly continuous manner through intermediation of a connection surface 36. That is, the outer surface of the main body 31 is smoothly processed so as to avoid damaging the intraoral cavity 71.

The main body 31 may include scale divisions 37. The scale divisions 37 are arranged along the longitudinal direction of the main body 31, and function as a guide indicating how deep the main body 31 is inserted into the intraoral cavity 71. The scale divisions 37 may be provided on any one of the outer peripheral surface or inner peripheral surface of the main body 31. When the scale divisions 37 are provided on the outer peripheral surface, it is preferred that, as illustrated in FIG. 2, the scale divisions 37 be provided on a side with which an upper lip and upper anterior teeth 75 are brought into contact, that is, on the upper side. The scale divisions 37 may be arranged at predetermined intervals (for example, in increments of 1 cm). In addition, the scale divisions 37 illustrated in FIG. 2 each have a length of nearly half a circumference in the circumferential direction of the main body 31, but are not limited thereto, and may be shorter or longer than the length.

In this embodiment, as an example of the scale divisions 37, a plurality of raised portions aligned along the longitudinal direction of the main body 31 are assumed. It is preferred that surfaces of the raised portions be smoothly processed so as to avoid damaging an oral cavity of the determination target person 7. However, for example, the scale divisions 37 may be a substantially linear protruding portion extending in the longitudinal direction on the outer peripheral surface of the main body 31, or may be printed or displayed on the outer peripheral surface or inner peripheral surface of the main body 31.

As illustrated in FIG. 3, the end portion 32 has an opening 32A, and the imaging device 57 can be inserted into the opening 32A. Therefore, the imaging device 57 is inserted into the main body 31 from the opening 32A, and is taken out of the main body 31 from the opening 32A.

The end portion 32 may be provided with the flange portion 34. The flange portion 34 extends from the end portion 32 toward the outside of the main body 31 in a radial direction thereof. When the main body 31 enters deep into the intraoral cavity 71, the flange portion 34 is brought into contact with lips or anterior teeth of the determination target person 7, to thereby prevent the determination target person 7 from accidentally ingesting the intraoral imaging assistance tool 3. In short, the flange portion 34 functions as a stopper.

In this embodiment, the flange portion 34 is provided over the entire circumference of the end portion 32, but may be partially formed at, for example, portions corresponding to the upper lip and lower lip in the end portion 32. In addition, an outer edge of the flange portion 34 may be a perfect circle as illustrated in FIG. 2, an elliptical shape, or a quadrangle or another polygonal shape.

For example, when the determination target person 7 coughs, the flange portion 34 is hit by a splash from the mouth of the determination target person 7. That is, the flange portion 34 also helps the doctor to avoid splashes from the determination target person 7. In order to provide this splash-proof function, the shape and dimensions of the flange portion 34 may be appropriately selected depending on, for example, an age of use or a physique.

The end portion 33 may also be open to form a window portion 33A. The window portion 33A is formed to provide a field of view from the inside of the main body 31 to the outside of the main body 31, and in this case, a lens of the imaging device 57 in the main body 31 is exposed to the outside. However, the window portion 33A may be covered with, for example, a transparent member, and this transparent member may be integrally molded with the main body 31 or may be molded separately from the main body 31. It is desired that a member covering the window portion 33A be made of a material subjected to an anti-fog process or measure or a material that does not easily fog in order to prevent fog due to a temperature in the inside of the mouth of the determination target person 7 or his or her breath. The examples of the anti-fog process and measure include anti-fog coating on the member covering the window portion 33A and a method of raising a temperature of the member covering the window portion 33A through use of a heating wire or another heat source, but the present invention is not limited thereto.

The end portion 33 protrudes toward the inside of the main body 31 to form the regulating portion 35. The regulating portion 35 is provided to regulate passage of the imaging device 57 in the main body 31 through the end portion 33 by being brought into contact with the imaging device 57. However, the regulating portion 35 is not required to be provided at the end portion 33. For example, a guide portion 141 (recessed portion or groove), which is described later in relation to FIG. 6, is brought into contact with an engaging protrusion 57A of the imaging device 57 at a terminal end portion of the guide portion 141, and regulates the movement of the imaging device 57 to a depth side of the main body 31, and therefore plays the role of the regulating portion 35 as well.

When the image of the pharynx 72 is to be captured through use of the above-mentioned intraoral imaging assistance tool 3, as illustrated in FIG. 1, the user inserts the intraoral imaging assistance tool 3 into the intraoral cavity 71 of the determination target person 7. At this time, the main body 31 pushes the tongue 73 downward and the soft palate 74 upward. After that or at the same time, the user inserts the imaging device 57 into the main body 31. At this time, as illustrated in FIG. 4, none of the tongue 73 and the soft palate 74 is included in the field of view of the imaging device 57, or occupies only a small range of the field of view even when the tongue 73 and the soft palate 74 are included. Therefore, a satisfactory field of view of the pharynx 72 can be obtained.

Further, the flange portion 34 can prevent the determination target person 7 from accidentally ingesting the intraoral imaging assistance tool 3. At the same time, the flange portion 34 can suppress scattering of splashes from the mouth of the determination target person 7 to the user, and can reduce a risk of secondary infection of influenza or another infectious disease to the user.

Further, the scale divisions 37 enable the intraoral imaging assistance tool 3 to be arranged at an appropriate oral cavity depth in accordance with the physique of the determination target person 7 and a site to be imaged. This contributes to acquisition of a clear image of the intended site, and can suppress discomfort and stifling of the determination target person 7 due to the insertion of the main body 31 deeper than required.

2-2 Modification Example 1 of Intraoral Imaging Assistance Tool

Figure 5:
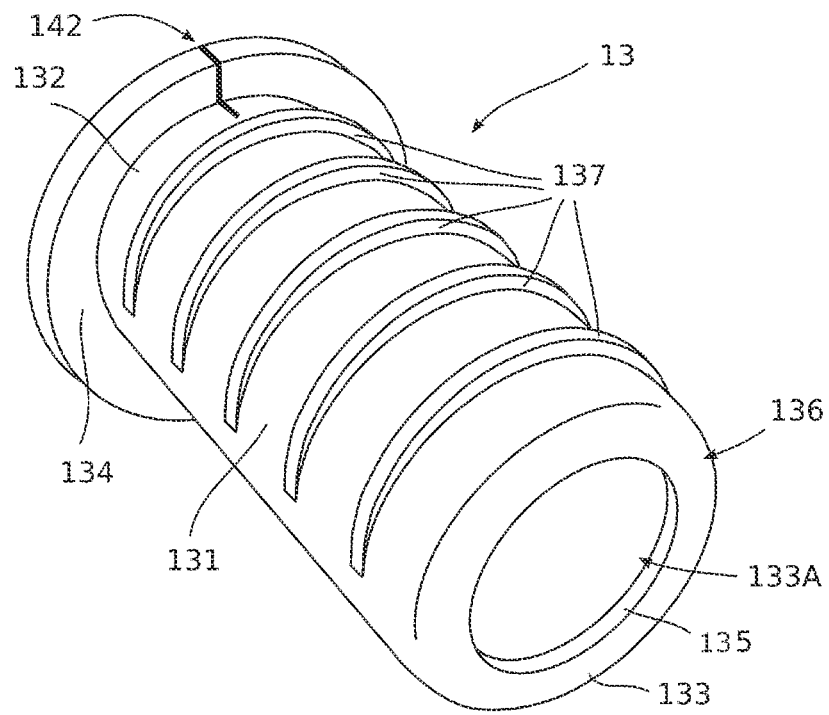
FIG. 5 is a perspective view for illustrating an intraoral imaging assistance tool (13) in Modification Example 1.
Figure 6:
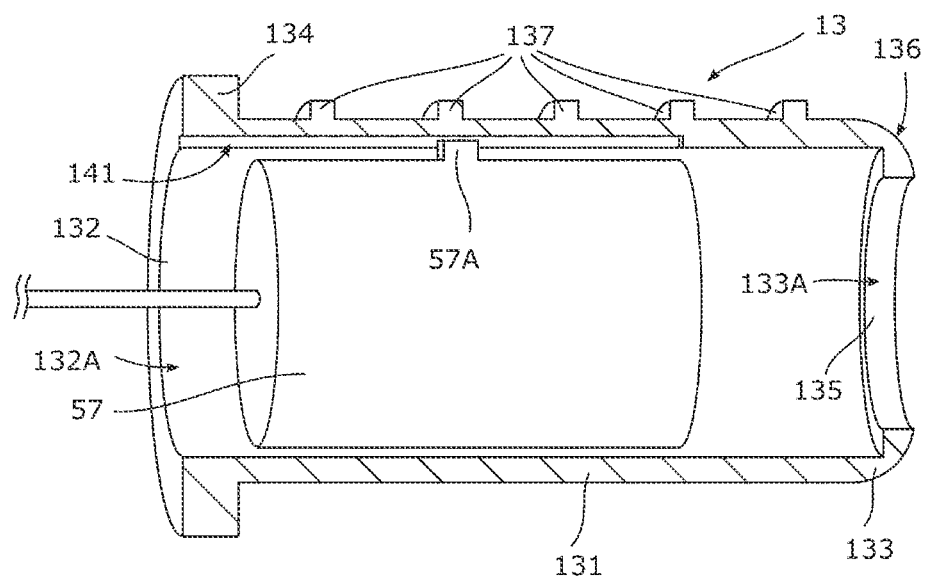
FIG. 6 is a longitudinal sectional view for illustrating the intraoral imaging assistance tool (13) of FIG. 5.
Figure 7:
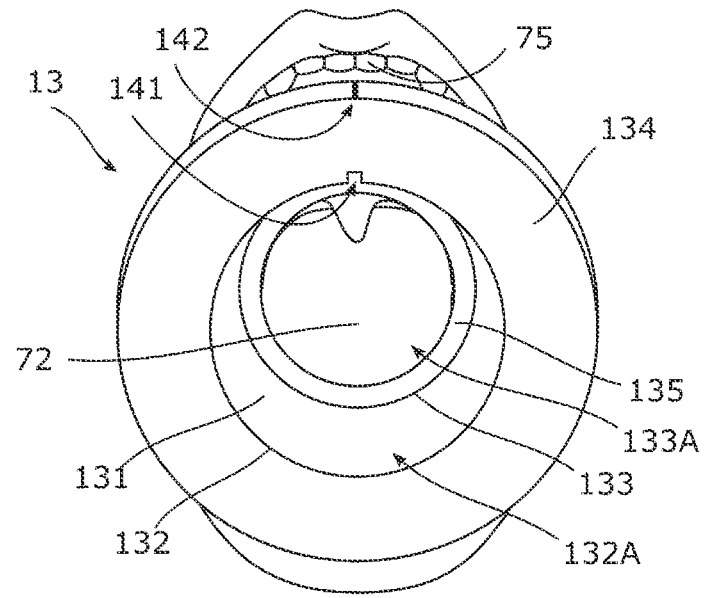
FIG. 7 is a view for illustrating an example of a state in which the intraoral imaging assistance tool (13) of FIG. 5 is inserted into the intraoral cavity (71).

Referring to FIG. 5 to FIG. 7, an intraoral imaging assistance tool 13 in Modification Example 1 of this embodiment is described.

The intraoral imaging assistance tool 13 includes the same types of components as those of the intraoral imaging assistance tool 3 described above, and further includes the substantially linear guide portion 141. Meanwhile, the imaging device 57 includes the engaging protrusion 57A which engages with the guide portion 141. Therefore, the guide portion 141 enables the imaging device 57 to slide in a main body 131 without rotating with respect to the main body 131.

In Modification Example 1, as illustrated in FIG. 6, an example of the guide portion 141 is a groove that substantially linearly extends from an end portion 132 to an end portion 133 so as to correspond to the engaging protrusion 57A on the outer peripheral surface of the imaging device 57. In another case, the guide portion 141 may be a pair of rails protruding from the inner peripheral surface of the main body.

When the cross-sectional shape of the main body 131 is selectively an elliptical shape, a polygonal shape, or an asymmetrical shape, for example, a substantially D-shape, and the imaging device 57 has an outer shape corresponding to the cross-sectional shape of the main body 131, the imaging device 57 can slide in the main body 131 without rotating with respect to the main body 131, and hence the inner peripheral surface of the main body 131 in this case also functions as a guide portion.

As illustrated in FIG. 5, the outer surfaces of the main body 131 and a flange portion 134 are provided thereon with an instruction indication 142 for facilitating positioning of the main body 131 with respect to the lips of the determination target person 7. As illustrated in FIG. 7, for example, the instruction indication 142 may be arranged at a position corresponding to a central portion of the upper lip of the determination target person 7 or corresponding to the upper anterior teeth 75, that is, at the center of the upper portion. For example, when the user attaches the intraoral imaging assistance tool 3 to the intraoral cavity 71 with the instruction indication 142 being aligned with the center of the upper lip of the determination target person 7, the images acquired by the imaging device 57 are aligned in substantially the same orientation. This facilitates machine learning and processing for determining presence or absence of a specific disease (for example, influenza) which are performed through use of images.

2-3 Modification Example 2 of Intraoral Imaging Assistance Tool

Figure 8:
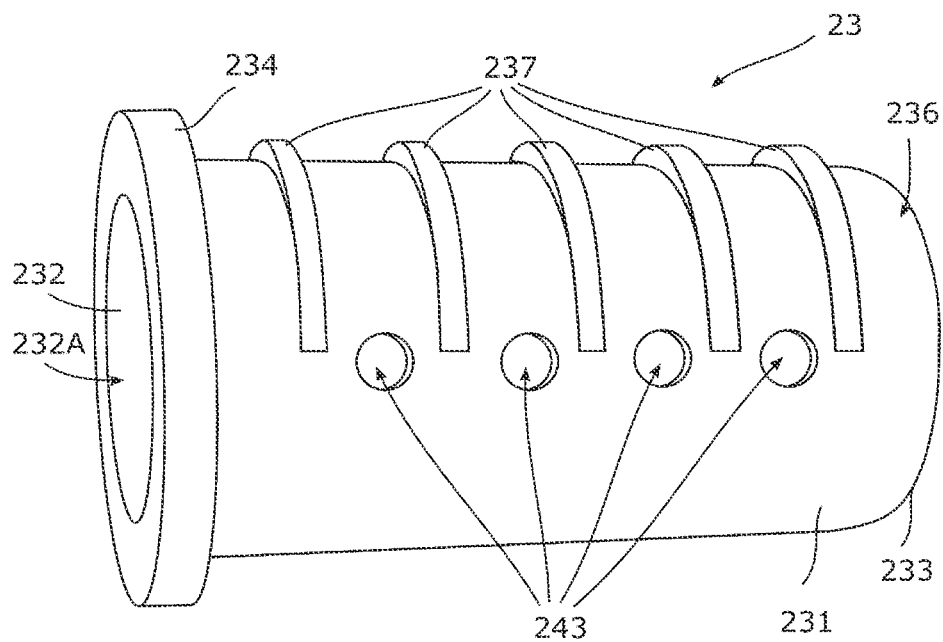
FIG. 8 is a perspective view for illustrating an intraoral imaging assistance tool (23) in Modification Example 2.

Referring to FIG. 8, an intraoral imaging assistance tool 23 in Modification Example 2 of this embodiment is described.

The intraoral imaging assistance tool 23 includes the same types of components as those of the intraoral imaging assistance tool 3 described above, and further includes at least one hole 243 in a main body 231. The hole 243 passes through a portion between the inside and outside of the main body 231. This hole 243 facilitates respiration performed by the determination target person 7 holding the intraoral imaging assistance tool 23 in his or her mouth, and can provide the determination target person 7 with a sense of security. A size of the hole 243, the number of holes 243, and arrangement thereof may be appropriately set so that saliva of the determination target person 7 does not easily enter therethrough.

The above-mentioned components in Modification Example 2, for example, the guide portion, can also be applied to the above-mentioned embodiment and Modification Example 1.

2-4 Modification Example 3 of Intraoral Imaging Assistance Tool

Figure 9:
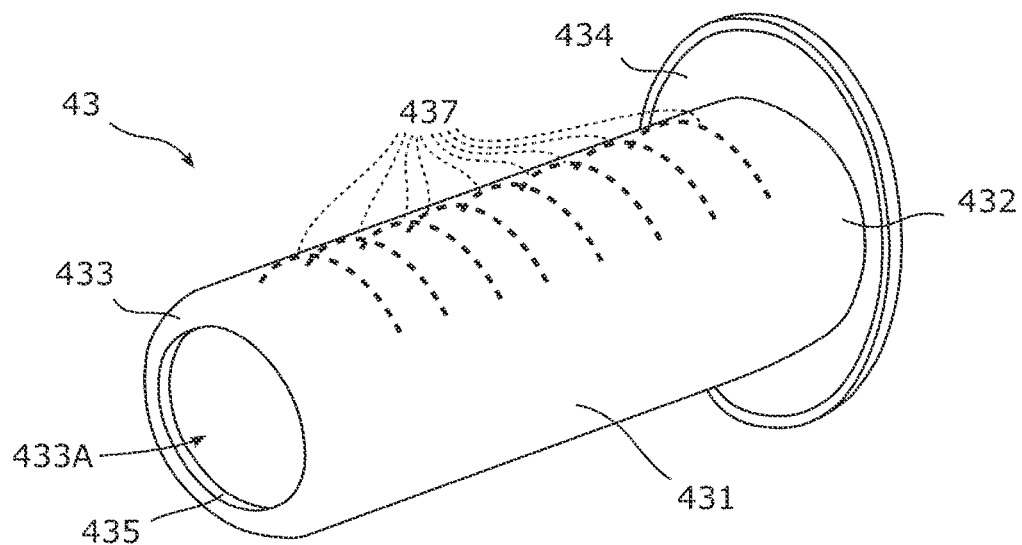
FIG. 9 is a perspective view of an intraoral imaging assistance tool (43) in Modification Example 3.
Figure 10:
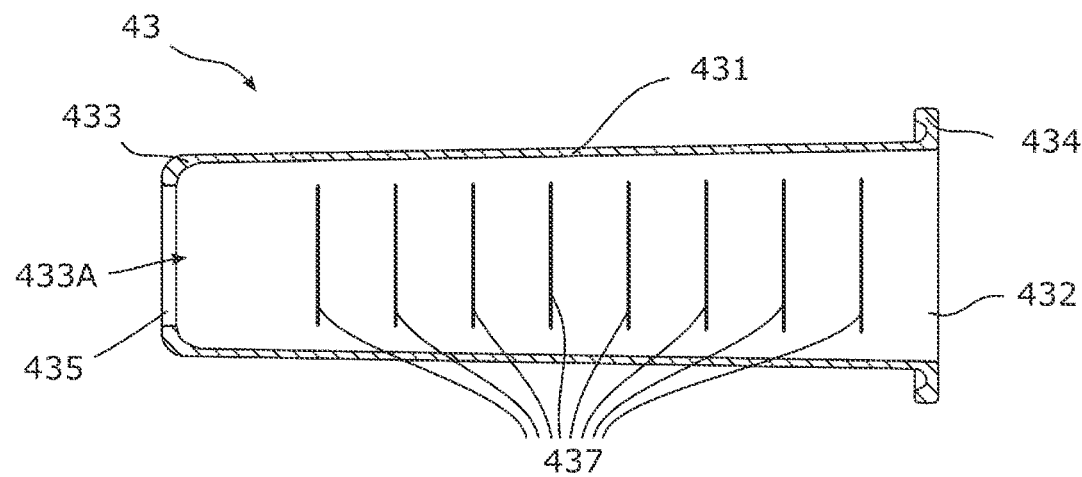
FIG. 10 is a transverse sectional view of the intraoral imaging assistance tool (43) of FIG. 9.

Referring to FIG. 9 and FIG. 10, an intraoral imaging assistance tool 43 in Modification Example 3 of this embodiment is described. The intraoral imaging assistance tool 43 includes the same types of components as those of the intraoral imaging assistance tool 3 described above.

A main body 431 of the intraoral imaging assistance tool 43 is a transparent or translucent resin molded product. Therefore, the imaging region of the intraoral imaging apparatus 5 is further expanded beyond a range visible from a window portion 433A, and hence a wider field of view can be obtained. In addition, the inner diameter of the main body 431 is slightly smaller at an end portion 433 than at an end portion 432, to thereby facilitate resin molding of the intraoral imaging assistance tool 43.

As illustrated in FIG. 10, the scale divisions 437 are formed on the inner peripheral surface of the main body 431, and hence the outer peripheral surface of the main body 431 can be smoothed. The scale divisions 437 may be protrusions protruding from the inner peripheral surface of the main body 431, or may be marks indicated on or applied to the inner peripheral surface.

As illustrated in FIG. 9, an outer edge of a flange portion 434 has an elliptical shape which is long in an up-down direction thereof, and thus positioning of the intraoral imaging assistance tool 43 with respect to the lips of the determination target person 7 is facilitated. The outer edge of the flange portion 434 also protrudes toward the end portion 433 or is formed to be thicker than other portions. Thus, required strength is ensured while an amount and cost of a material of the flange portion 434 are reduced.

2-5 Modification Example 4 of Intraoral Imaging Assistance Tool

Figure 11:
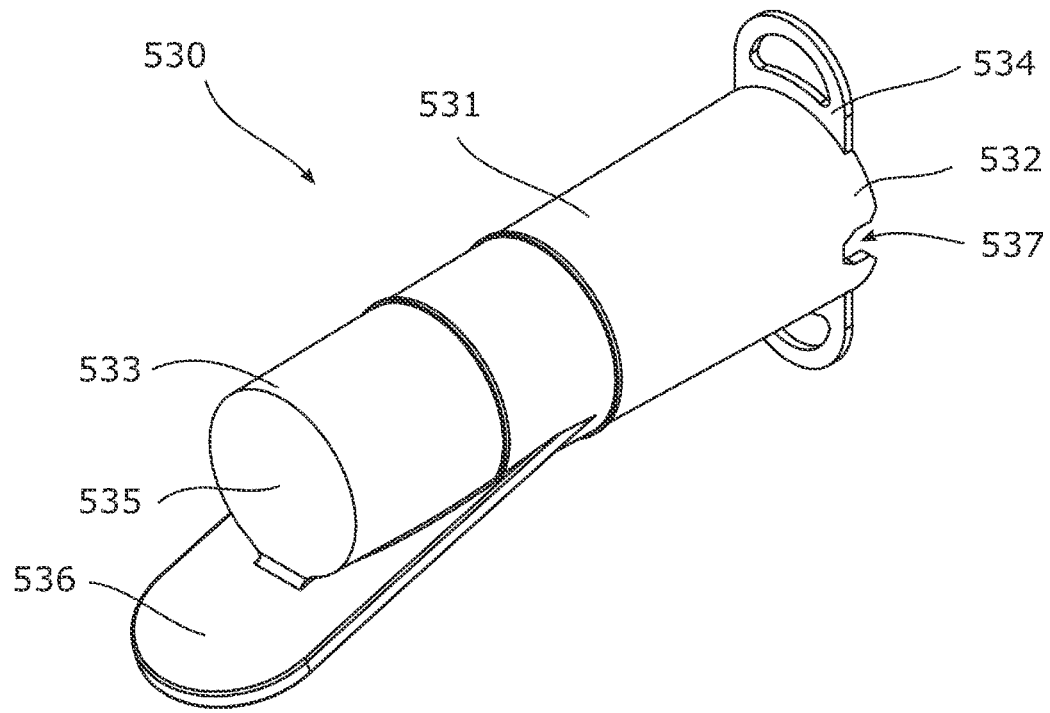
FIG. 11 is a perspective view of an intraoral imaging assistance tool (530) in Modification Example 4.
Figure 12:
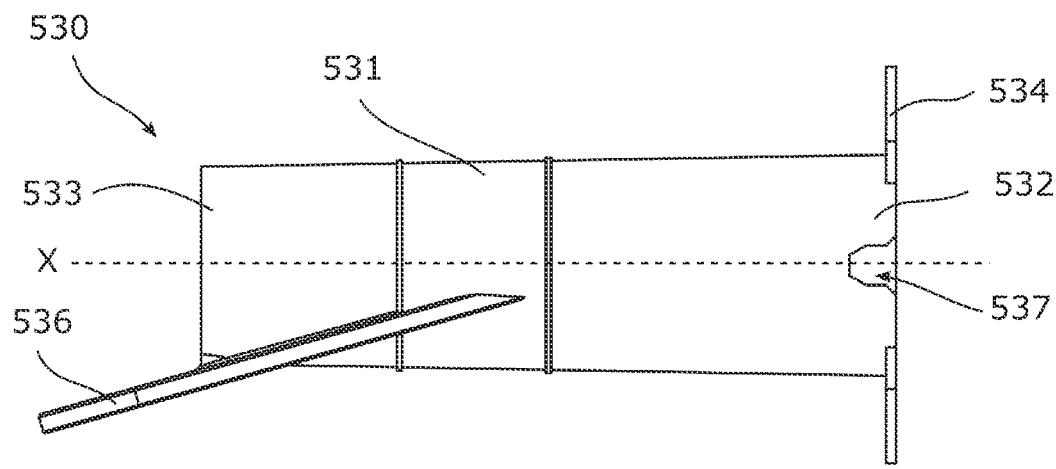
FIG. 12 is a side view of the intraoral imaging assistance tool (530) of FIG. 11.

Referring to FIG. 11 and FIG. 12, an intraoral imaging assistance tool 530 in Modification Example 4 of this embodiment is described. As illustrated in FIG. 11 and FIG. 12, the intraoral imaging assistance tool 530 includes a cylindrical main body 531 including end portions 532 and 533.

The end portion 532 is open to guide the imaging device 57 of the intraoral imaging apparatus 5 into the main body 531. The end portion 532 includes a pair of flange portions 534 protruding toward the outside of the main body 531, and also includes a notch 537 for positioning the intraoral imaging apparatus 5 by engaging with a protrusion provided on the intraoral imaging apparatus 5.

The end portion 533 on the opposite side includes a window portion 535 to be opposed to the imaging device 57 in the main body 531. In this case, the window portion 535 is assumed to be a transparent member covering the end portion 533, but the window portion 535 may be an opening formed in the end portion 533.

A depressing piece 536 extends from the main body 531. The depressing piece 536 plays the role of a tongue depressor for depressing the tongue 73 of the determination target person 7 so that the pharynx 72 of the determination target person 7 can be clearly viewed from the imaging device 57 in the main body 531. Therefore, as illustrated in FIG. 12, the depressing piece 536 is inclined so as to be spaced farther apart from an axial center X of the main body 531 toward the pharynx 72 side.

In this manner, the function of protecting the imaging device 57 and the function of the tongue depressor are assigned to the main body 531 and the depressing piece 536, respectively, and thus the intraoral imaging assistance tool 530 can be downsized. This alleviates a burden (for example, choking or suffocation) felt by the determination target person 7 when the intraoral imaging assistance tool 530 is attached, and improves convenience of the intraoral imaging assistance tool 530.

2-6 Modification Example 5 of Intraoral Imaging Assistance Tool

Figure 13:
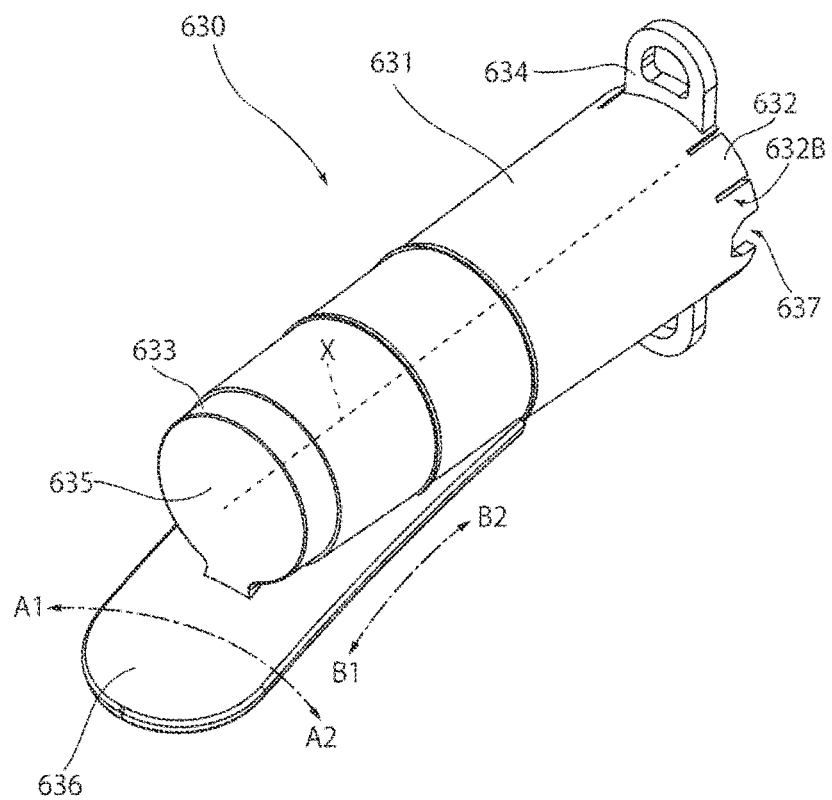
FIG. 13 is a perspective view of an intraoral imaging assistance tool (630) in Modification Example 5.
Figure 14:
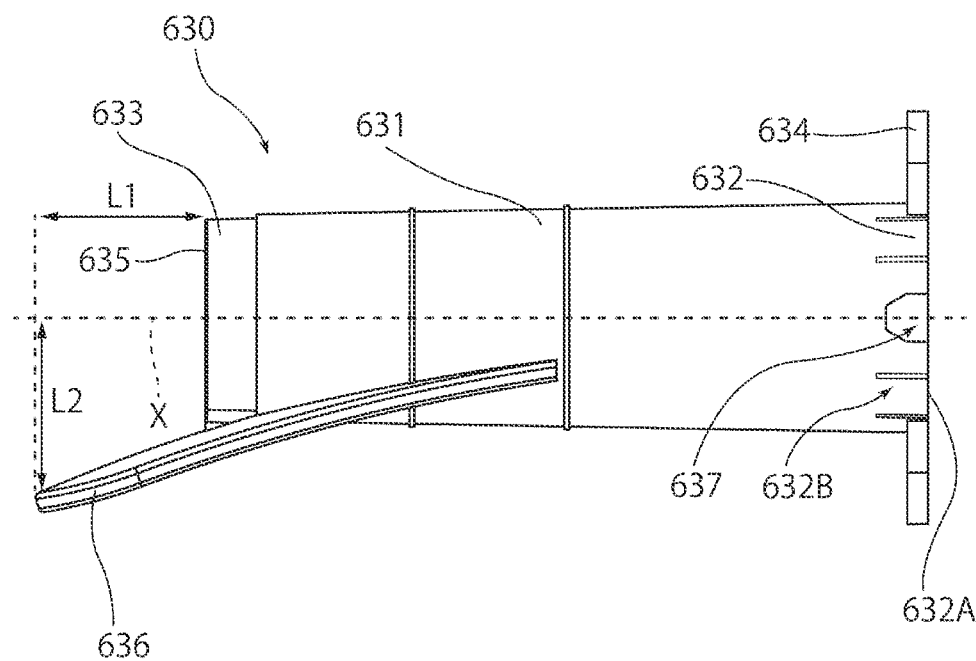
FIG. 14 is a side view of the intraoral imaging assistance tool (630) of FIG. 13.
Figure 15:
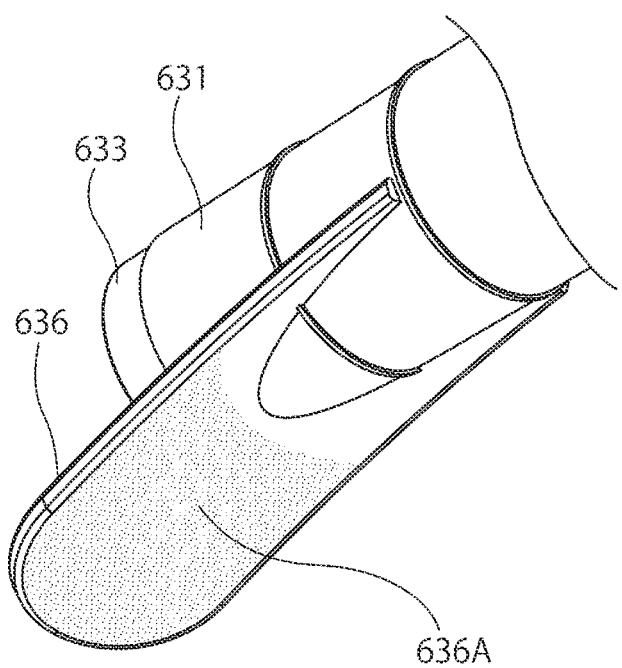
FIG. 15 is a perspective view of the intraoral imaging assistance tool (630) of FIG. 13 when viewed from the lower side.

Referring to FIG. 13, FIG. 14, and FIG. 15, an intraoral imaging assistance tool 630 in Modification Example 5 of this embodiment is described. As illustrated in FIG. 13, FIG. 14, and FIG. 15, the intraoral imaging assistance tool 630 includes a cylindrical main body 631 including end portions 632 and 633.

In the end portion 632, an opening 632A for guiding the imaging device 57 of the intraoral imaging apparatus 5 into the main body 631 is formed. The end portion 632 includes a pair of jaw portions 634 protruding toward the outside of the main body 631, and includes a notch 637 for positioning the intraoral imaging apparatus 5 by engaging with the engaging protrusion 57A (see FIG. 6) provided on the imaging device 57 of the intraoral imaging apparatus 5.

The end portion 633 positioned on the opposite side of the end portion 632 of the main body 631 includes a window portion 635 to be opposed to a tip end of the imaging device 57 when the imaging device 57 is inserted into the main body 631. The window portion 635 can be composed of, for example, a transparent member covering the end portion 633. However, a specific configuration of the window portion 635 is not particularly limited as long as the imaging device 57 arranged in the main body 631 can capture an image of the intraoral cavity 71 through the window portion 635. The window portion 635 may be, for example, an opening formed in the end portion 633.

In addition, when the window portion 635 is composed of a transparent member, for example, the window portion 635 may be composed of the same material as the material composing the main body 631, or may be composed through use of a material different from the material composing the main body 631. When the window portion 635 is composed of a material different from the material composing the main body 631, the window portion 635 can be composed to have physical properties different from physical properties of the material composing the main body 631. The material of the window portion 635 can be suitably selected from the viewpoints of, for example, the strength, translucency, cost, and degree of ease of manufacturing work that correspond to product specifications of the window portion 635.

The main body 631 can be manufactured by injection molding using a molding die when the main body 631 is to be composed of a resin material. As described above, when the window portion 635 is composed of a material different from the material composing the main body 631, it is possible to employ, for example, insert molding for injecting a resin material into a molding die under a state in which a transparent member is set in the molding die.

As illustrated in FIG. 13 and FIG. 14, an easily deformable portion 632B can be formed in the end portion 632 of the main body 631. The easily deformable portion 632B can be formed of, for example, a plurality of slits which are connected to the opening 632A, and extend substantially linearly from the opening 632A side to a tip end side (side on which the end portion 633 is positioned) of the main body 631. The plurality of slits can be arranged along a circumferential direction of the main body 631 at predetermined intervals. Each of the plurality of slits pass through the outer surface of the main body 631 and the inner surface of the main body 631. The number and specific shapes of slits are not particularly limited.

When the user inserts the imaging device 57 into the main body 631 through the opening 632A formed in the end portion 632, the user can deform the end portion 632 in such a manner that the end portion 632 is pushed to be expanded outwardly (in a direction farther apart from the axial center X) by the easily deformable portion 632B formed in the end portion 632. Therefore, the user can also easily insert the imaging device 57 into the main body 631 through the opening 632A formed in the end portion 632, for example, when the main body 631 is made of a hard material that is not easily deformed, when an outer shape (outer diameter) of the imaging device 57 is larger than an outer shape (inner diameter) of the opening 632A, or when the outer shape of the imaging device 57 and the outer shape of the opening 632A are different from each other.

A specific configuration of the easily deformable portion 632B is not limited as long as workability of the user at a time of inserting the imaging device 57 into the main body 631 can be improved. The easily deformable portion 632B may be formed of, for example, a thin portion in which a material thickness of the end portion 632 is made thinner than other portions of the main body 631, a flexible portion in which the end portion 632 is composed of a material more flexible than other portions of the main body 631, or a portion obtained by selectively combining those structures and the slits.

As illustrated in FIG. 13 and FIG. 14, the main body 631 includes a depressing piece 636 extending toward the tip end side of the main body 631.

In the same manner as the depressing piece 536 (see FIG. 12) included in the intraoral imaging assistance tool 530 in Modification Example 4, the depressing piece 636 depresses the tongue 73 of the determination target person 7 when the image of the intraoral cavity 71 is captured by the imaging device 57. The user can clearly view the pharynx 72 by pushing down the tongue 73 of the determination target person 7 by the depressing piece 636.

As illustrated in FIG. 14, the depressing piece 636 is inclined so as to be spaced farther apart from the axial center X of the main body 631 toward the pharynx 72 side. As indicated by the arrow A1-A2 of FIG. 13, the depressing piece 636 can be formed to have, for example, a shape that is convexly curved with respect to a direction (left-right direction in a front view of the main body 631) intersecting a protruding direction of the depressing piece 636. As indicated by the arrow B1-B2 of FIG. 13, the depressing piece 636 can also be formed to have, for example, a shape that is convexly curved with respect to the protruding direction of the depressing piece 636.

When the intraoral imaging assistance tool 630 is used to assist in imaging of the intraoral cavity 71, the user presses the depressing piece 636 formed in a curved shape against the tongue 73 of the determination target person 7, to thereby be able to fit the depressing piece 636 into a rounded shape of the tongue 73. Therefore, the user can inhibit the depressing piece 636 from being displaced from the tongue 73 while the intraoral imaging assistance tool 630 is used. In addition, the depressing piece 636 is placed along the rounded shape of the tongue 73 while the depressing piece 636 is pressed against the tongue 73, and hence a sense of discomfort felt on the tongue 73 by the determination target person 7 is alleviated.

When the depressing piece 636 is formed in a shape that is convexly curved with respect to each of the direction intersecting the protruding direction of the depressing piece 636 and the protruding direction of the depressing piece 636, a curvature of the depressing piece 636 in each of the directions is not particularly limited.

The depressing piece 636 may be formed so as not to be included in a viewing angle of the imaging device 57 while the intraoral imaging assistance tool 630 is being used to assist in the imaging of the intraoral cavity 71 of the determination target person 7, or may be formed so as to be included in the viewing angle of the imaging device 57. When the depressing piece 636 is formed so as not to be included in the viewing angle of the imaging device 57, the depressing piece 636 does not appear in the captured image, and hence a clear image of the pharynx 72 can be acquired. Meanwhile, when the depressing piece 636 is formed so as to be included in the viewing angle of the imaging device 57, the user can visually confirm the position of the depressing piece 636 during the imaging, and therefore can proceed with work with a sense of security.

As illustrated in FIG. 15, it is possible to form, on a lower surface (surface on the tongue side) of the depressing piece 636, a slip suppressing portion 636A for inhibiting the depressing piece 636 from being displaced from the tongue 73 when the depressing piece 636 is placed on the tongue 73 of the determination target person 7.

The slip suppressing portion 636A can be composed of, for example, an uneven portion formed by an embossing process. The uneven portion formed by the embossing process prevents the depressing piece 636 from being displaced from the tongue 73 by increasing a frictional force generated between the tongue 73 and the lower surface of the depressing piece 636. A specific configuration of the slip suppressing portion 636A is not limited as long as the slip suppressing portion 636A can prevent the depressing piece 636 from being displaced from the tongue 73. The slip suppressing portion 636A can also be formed of, for example, a coating for increasing the frictional force, grooves having an uneven shape, a site formed to have a large surface roughness, or a combination of those. Further, for example, the slip suppressing portion 636A may be formed on the entire lower surface of the depressing piece 636, or may be formed only on a part of the lower surface of the depressing piece 636.

For example, a design (for example, character), a texture pattern, a color, a mark, a scent, a taste, or a suitable combination of those can be added to the depressing piece 636. Through employment of such a configuration as described above, for example, when the determination target person 7 is a child, it is possible to alleviate anxiety or stress felt by the determination target person 7. The above-mentioned design or the like may be added to the main body 631.

2-7 Other Modification Examples of Intraoral Imaging Assistance Tool

The main body 31 is not required to have substantially the same inner diameter over a range from the end portion 32 to the end portion 33. For example, the main body 31 may be configured to have the inner diameter increasing toward the end portion 32. Such a bell-shaped main body 31 enables stacking of a plurality of intraoral imaging assistance tools 3, and hence space for transportation and storage can be reduced.

The intraoral imaging assistance tool 3 is also assumed to be an integrally molded resin product, but may be made of, for example, rubber or another elastic material, or may be designed to be attached to the intraoral imaging apparatus 5 so as to cover all or a part thereof in the same manner as a condom.

Further, as the imaging device 57, a camera mounted on a smartphone or a tablet terminal may be employed. In order to fix a positional relationship between the camera and the intraoral imaging assistance tool 3 (opening 32A), a frame or a clip may be provided on the main body 31 or the flange portion 34. For example, the intraoral imaging assistance tool 3 may be provided with a clip for sandwiching the smartphone from an upper edge or lateral edge thereof, or an L-shaped frame for being pressed against a corner of the smartphone.

The structures of the intraoral imaging assistance tools described in the embodiment and the modification examples can be appropriately combined as long as the essential functions of the intraoral imaging assistance tools are not impaired.

2-8 Packaging Example of Intraoral Imaging Assistance Tool

Figure 16:
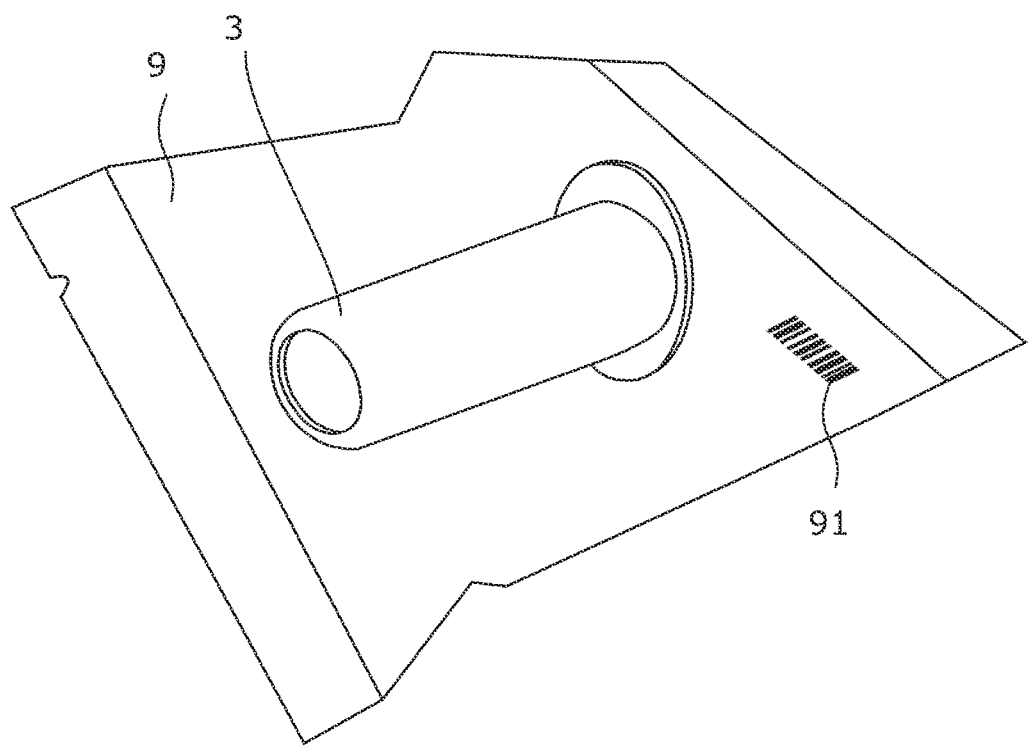
FIG. 16 is a schematic view for illustrating the intraoral imaging assistance tool (3) that has been packaged.

The intraoral imaging assistance tool 3 may be sterilized and individually packaged in a pouch 9 on which an identifier 91 is displayed as illustrated in FIG. 16, to thereby enable hygienic management of the intraoral imaging assistance tool 3. The identifier 91 may be displayed on the intraoral imaging assistance tool 3.

The identifier 91 includes identification information including, for example, a product ID of the intraoral imaging assistance tool 3. Examples of the identifier 91 include a bar code and an RF tag, and the bar code is preferred in consideration of reading by the intraoral imaging apparatus 5 and use of the medical apparatus 1 in a medical institution. As the bar code, any one of a one-dimensional bar code or a two-dimensional bar code can be used.

For example, an image of the identifier 91 is captured by the imaging device 57 before the intraoral imaging, and the identification information on the intraoral imaging assistance tool 3 in the pouch 9 is read onto the intraoral imaging apparatus 5, and thus lot information on the corresponding intraoral imaging assisting tool 3 can be confirmed. Thus, traceability can be ensured even when an adverse event occurs to the patient due to contact with the oral cavity. It is also possible to detect reuse of the intraoral imaging assistance tool 3, and hence it is possible to prevent contamination and secondary infection due to the reuse and ensure safety from a hygienic perspective.

3-1 Intraoral Imaging Apparatus

Referring to FIG. 17 to FIG. 25, the intraoral imaging apparatus 5 is described in detail.

Figure 18:
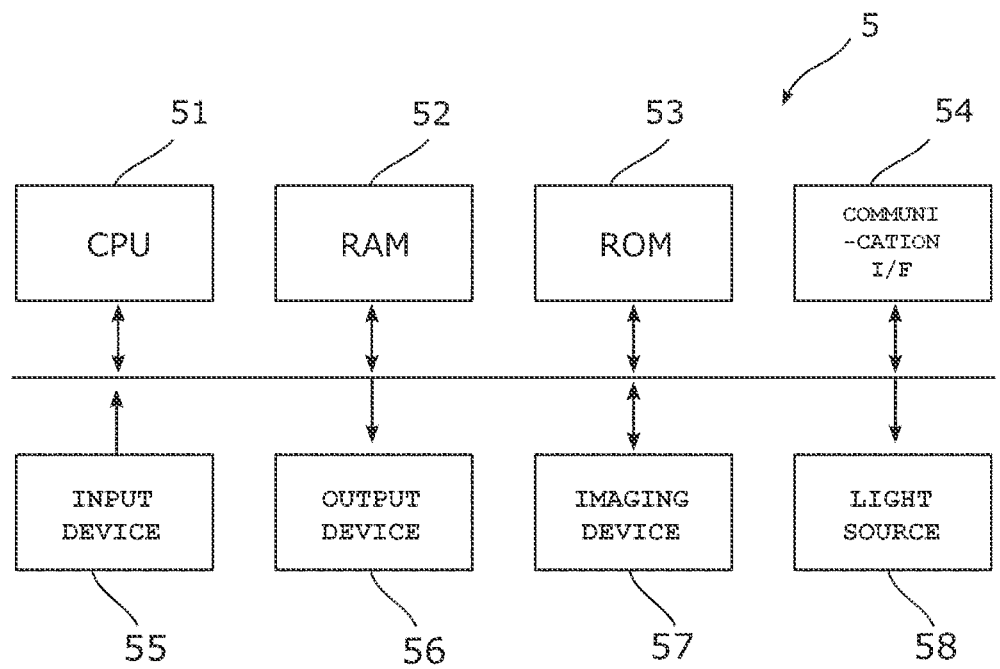
FIG. 18 is a block diagram for illustrating an example of a hardware configuration of the intraoral imaging apparatus (5) of FIG. 9.

The intraoral imaging apparatus 5 is a computer including an imaging device, an arithmetic unit, and storage devices. In this case, it is assumed that the intraoral imaging apparatus 5 is formed of one computer, but the intraoral imaging apparatus 5 may be formed of a plurality of computers. For example, in remote diagnostic imaging, the imaging function and the determination function may be executed by separate computers. As illustrated in FIG. 18, the intraoral imaging apparatus 5 includes the imaging device 57, a central processing unit (CPU) 51 serving as an example of the arithmetic unit, a random access memory (RAM) 52 and a read-only memory (ROM) 53 which serve as examples of the storage devices, a communication interface 54, an input device 55, an output device 56, and a light source 58.

The communication interface 54 is a wired or wireless communication module, and is used, for example, for acquiring and updating an application program and a determination algorithm and for collecting (transmitting) the captured images. Assumed examples of the wireless communication interface include devices conforming to any one of a wireless LAN standard such as Wi-Fi, a short-range wireless communication standard such as Bluetooth (trademark), or a third-generation/fourth-generation mobile communication standard, but the present invention is not limited thereto.

Figure 17:
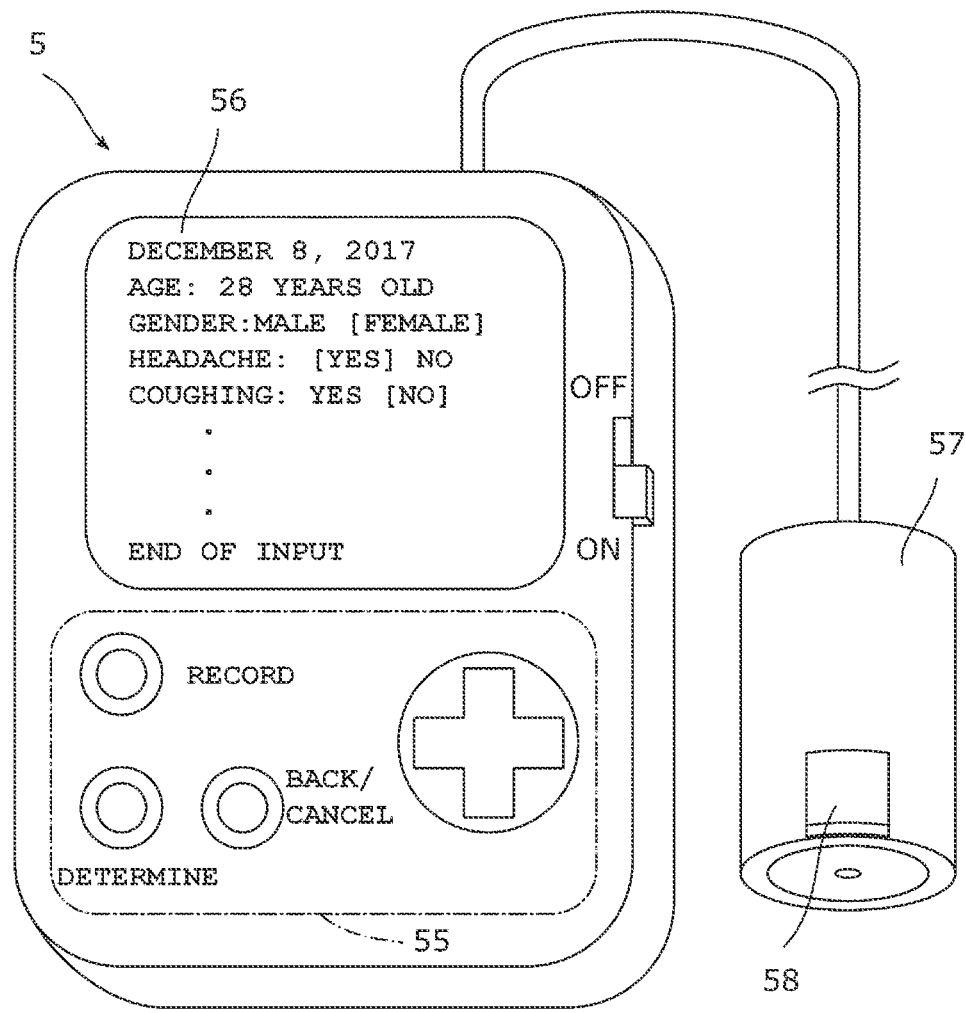
FIG. 17 is a view for illustrating an example of an outer appearance of the intraoral imaging apparatus (5) of FIG. 1.

The input device 55 is an example of an input device for receiving user input, and examples thereof include various operation buttons and operation keys as illustrated in FIG. 17. In another case, the input device 55 may be, for example, a touch panel, a microphone, an operation dial, a stylus, or another input means. The input device 55 may be arranged in the main body (casing) of the intraoral imaging apparatus 5, or may be arranged in, for example, the imaging device 57.

The output device 56 is an example of an output device for outputting a determination result, and examples thereof include a display, a speaker, and a printer.

The imaging device 57 acquires an image. In this embodiment, a moving image is assumed as an image to be acquired by the imaging device 57. It suffices that the image to be acquired has an image size of, for example, 640×480 pixels and a frame rate of, for example, 30 fps. However, the image size and the frame rate are not limited thereto.

The imaging device 57 may be capable of selectively or additionally capturing a still image. When the still image is to be captured, it is desired that the imaging device 57 have a continuous shooting function, but the present invention is not limited thereto.

In this embodiment, as illustrated in FIG. 17, it is assumed that the imaging device 57 is provided separately from the main body (casing) of the intraoral imaging apparatus 5 to be inserted alone into the intraoral imaging assistance tool 3. It is preferred that the imaging device 57 also have an outer shape (for example, cylindrical shape) corresponding to the inner peripheral surface of the main body 31 of the intraoral imaging assistance tool 3.

However, the imaging device 57 may be incorporated into the main body of the intraoral imaging apparatus 5 in the same manner as, for example, a smartphone or a tablet terminal.

The imaging device 57 may have an autofocus mechanism (not shown) to be set so that, for example, a specific site is in focus in front of the lens. The imaging device 57 may also have a function of automatically recognizing a specific site (for example, posterior pharyngeal wall) and focusing on the specific site. The imaging device 57 may also have a zoom function to be set to perform imaging at an appropriate magnification depending on, for example, dimensions of the posterior pharyngeal wall or follicles.

While the imaging device 57 is operating, light may be emitted from the light source 58 toward a subject, to thereby ensure an image having satisfactory quality. In this case, the light emitted by the light source 58 may be visible light, or may be non-visible light, for example, near infrared rays or infrared rays. In addition, each of a plurality of light sources 58 may be in charge of application of light having a wavelength in a specific range so that, for example, one light source applies visible light while another light source applies near infrared rays or infrared rays.

Meanwhile, it suffices that the imaging device 57 includes a type and number of light-receiving elements capable of appropriately receiving the light emitted from the light source 58. For example, it suffices that, when the light source 58 emits visible light, the imaging device 57 includes a light-receiving element suitable for receiving the visible light, and when the light source 58 emits non-visible light, the imaging device 57 includes a light-receiving element suitable for receiving the non-visible light. For example, the light source may be a light emitting diode (LED) or may use organic electroluminescence (OEL).

Selectively, programming may be performed so that the image being captured and a translucent illustration are superimposed on each other on the display serving as the output device 56 while the imaging device 57 is operating. When the user moves the imaging device 57 so that the illustration and the image of the corresponding site (for example, uvula or palatine tonsil) are superimposed on each other, it is possible to obtain an appropriate image for determination.

The ROM 53 stores an application program for executing various kinds of processing in the intraoral imaging apparatus 5 and an algorithm for determining a specific disease. The ROM 53 may also store the image acquired by the imaging device 57, the identification information on the intraoral imaging assistance tool 3, various kinds of information input from the input device 55 (for example, information of the determination target person 7), and the determination result. The ROM 53 may be a device of a built-in type or a removable type, for example, a USB flash drive or a MicroSD card, and may further include a storage area of a storage device of an external server or another external computer.

The CPU 51 can read the application program stored in the ROM 53 onto the RAM 52 and execute various kinds of processing including Processing (a) to Processing (d). When the image acquired by the imaging device 57 is a single still image, extraction processing may be omitted.

3-2 Main Processing Executed by CPU (a) Extraction Processing

The CPU 51 extracts at least one still image satisfying a predetermined condition from the images acquired from the imaging device 57. For example, when the imaging device 57 captures a moving image, the CPU 51 extracts at least one still image from among a plurality of still images included in the moving image. When a moving image is to be captured, still images are recorded at a predetermined frame rate. The still images are supposed to include those with satisfactory imaging conditions and those with poor imaging conditions. As the images to be used in the next determination processing, several images with satisfactory imaging conditions are selected.

For example, such a condition that accuracy of diagnosis and determination of a specific disease (for example, influenza) is high when all or a part of a specific imaging angle, a specific degree of irradiation with light, a specific width of the field of view, a drawing position of a specific site (for example, pharynx), and a degree of focus on the specific site are satisfied is found in advance based on a large amount of similar image data, and the condition is used as a criterion for judging whether the imaging conditions are satisfactory or poor. When such a criterion is employed, as illustrated in, for example, FIG. 23, the extraction processing includes procedural steps of: ranking images based on the drawing position of an imaging target (Step S31); ranking the images based on the degree of focus on the specific site (Step S32); ranking the images based on the state of irradiation with light (Step S33); and finally selecting several images that are ranked higher in the overall ranking (Step S34). Before the calculation of the overall ranking, the images may be additionally ranked based on criteria of the width of the field of view or the imaging angle. In another case, a deep learning function may be used for the extraction processing.

(b) Determination Processing

The CPU 51 determines a possibility of a specific disease based on the image acquired from the imaging device 57 (for example, at least one still image obtained by the extraction processing) and the determination algorithm stored in the ROM 53. The specific disease is influenza in this embodiment. For the determination, information on the determination target person 7 (hereinafter referred to as "patient information") input by the user through use of the input device 55 or acquired by another method may be used in combination. The patient information includes, for example, an age, a gender, a time elapsed since onset, presence or absence of influenza symptoms (for example, coughing, runny nose, and chills), and a history of contact with other influenza patients. The patient information may include all or a part of racial and genetic information, a date and season, location information (latitude and longitude of a place of consultation), meteorological information (for example, weather and temperature), and information on a level of influenza pandemic in a certain area at a certain time.

Figure 22:
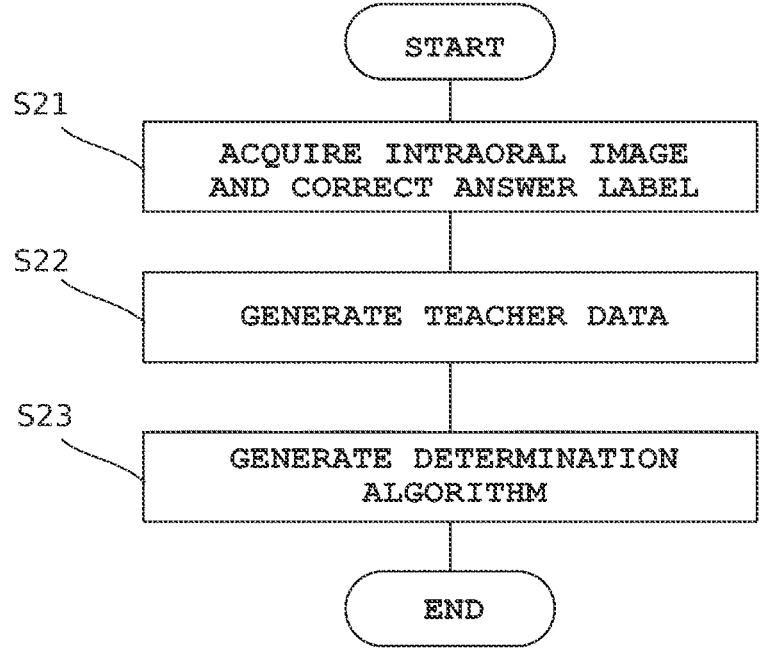
FIG. 22 is a flow chart for illustrating a procedure for generating a determination algorithm.
Figure 23:
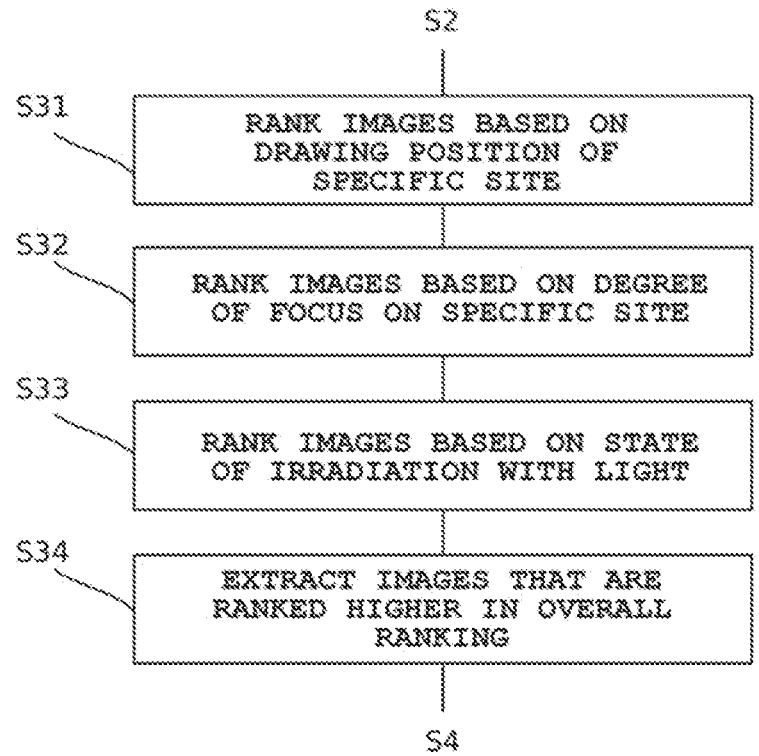
FIG. 23 is a flow chart for illustrating an example of an image extraction procedure.

In this case, the determination algorithm may be generated by a procedure illustrated in, for example, FIG. 22.

For example, in a case of influenza, pharyngeal images of patients and correct answer labels that are attached thereto and indicate whether or not the patients are infected with influenza are first collected in a medical institution (Step S21). The correct answer labels are given based on, for example, results of swab-based rapid influenza tests, PCR tests, and virus isolation culture tests that have been taken by the patients. The PCR test and the virus isolation culture test require several weeks for outcome of results, but exhibit extremely high accuracy, and hence the results are suitable as correct answer labels. In addition, the correct answer label may include not only the image data but also the above-mentioned patient information.

Subsequently, teacher data (image data) labeled with the determination result of the above-mentioned PCR test or virus isolation culture test as a correct answer is generated (Step S22). Machine learning is performed based on this teacher data to generate a determination algorithm (Step S23). This determination algorithm is an algorithm for determining, when an image is given, whether or not the image is likely to indicate influenza. Thus, it is possible to quantify a possibility that the image indicates influenza, and to achieve an indication of, for example, "98.5%."

Whether the patient is positive or negative may be selectively determined as in, for example, "Determined as: Influenza Positive" or "Determined as: Influenza Negative." In this case, in addition to the positive or negative determination, reliability of the determination may be quantified or indicated by a graded evaluation of, for example, high, medium, or low. In another case, a degree of certainty of influenza may be indicated by the graded evaluation of, for example, high, medium, or low.

(c) Output Processing

The CPU 51 outputs a result of the determination processing. Examples of an output method include an indication on a display and transmission to another computer.

(d) Acquisition of Identification Information on Intraoral Imaging Assistance Tool The CPU 51 may selectively request the user to input the identification information on the intraoral imaging assistance tool 3 to be used for new determination prior to the determination. For example, when the user captures an image of the identifier 91 by the imaging device 57, the CPU 51 acquires the identification information on the corresponding intraoral imaging assistance tool 3 from the image of the identifier 91.

Subsequently, the CPU 51 searches records in the ROM 53 to examine presence or absence of a record that matches the corresponding intraoral imaging assistance tool 3. In another case, the CPU 51 may cause an external server to examine records of use of the intraoral imaging assistance tool 3 on the external server.

When there is no matching record, the CPU 51 allows new determination. When there is a matching record, the CPU 51 determines that the corresponding intraoral imaging assistance tool 3 has been used. Then, the CPU 51 may, for example, display an alarm on the display or end a series of processing steps. That is, the CPU 51 can limit the new determination based on search results.

3-3 Functional Configuration of Intraoral Imaging Apparatus

Figure 19:
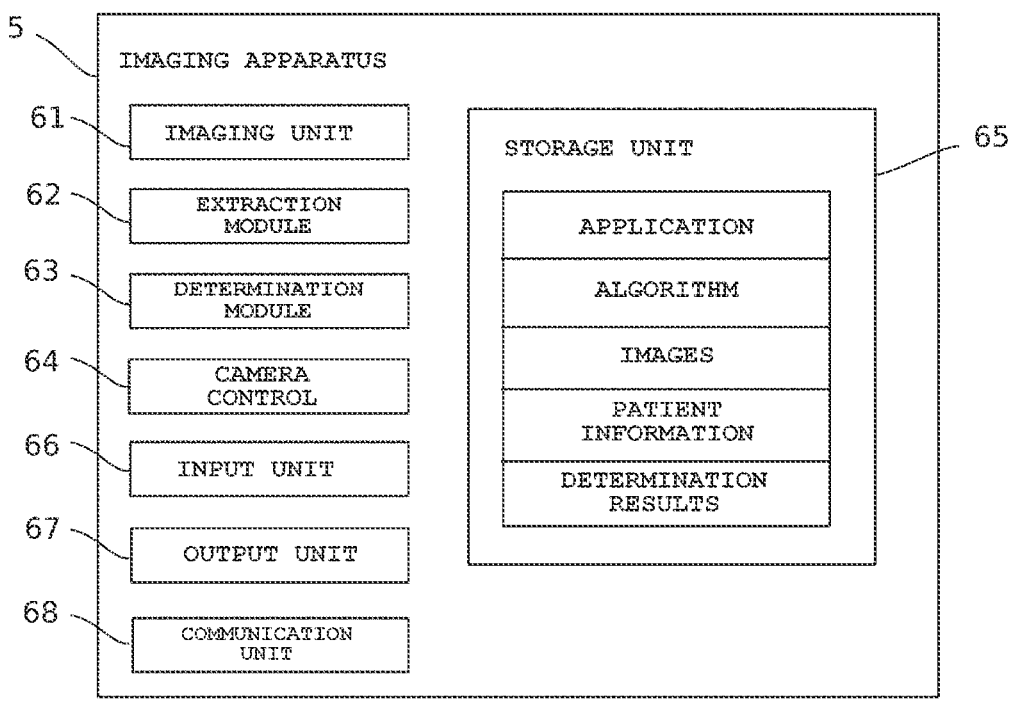
FIG. 19 is a block diagram for illustrating an example of a functional configuration of the intraoral imaging apparatus (5) of FIG. 9.

FIG. 19 is an illustration of a functional configuration of the intraoral imaging apparatus 5. The intraoral imaging apparatus 5 includes an imaging unit 61, an extraction module 62, a determination module 63, a camera control 64, a storage unit 65, an input unit 66, an output unit 67, and a communication unit 68. To indicate correspondence relationships with the hardware configuration of the intraoral imaging apparatus 5, the imaging unit 61 corresponds to the imaging device 57, the extraction module 62, the determination module 63, and the camera control 64 correspond to the CPU 51, the storage unit 65 corresponds to the ROM 53, the input unit 66 corresponds to the input device 55, the output unit 67 corresponds to the output device 56, and the communication unit 68 corresponds to the communication interface 54. In this case, the camera control 64 controls the imaging device 57 to implement an autofocus function, a zoom function, and other various functions.

As other functions, the intraoral imaging apparatus 5 may have a timekeeping function of acquiring a time at which the imaging has been performed, a location information acquisition function of acquiring information on a location at which the imaging has been performed, and a meteorological information acquisition function of acquiring the meteorological information at the location. The timekeeping function may be implemented as a built-in clock, or may be a function of a communication interface for accessing an external time server. The location information acquisition function may be implemented as, for example, a global positioning system (GPS). The meteorological information acquisition function may be a function of a communication interface for accessing an external meteorological server.

3-4 Operation Example 1 of Intraoral Imaging Apparatus

Figure 20:
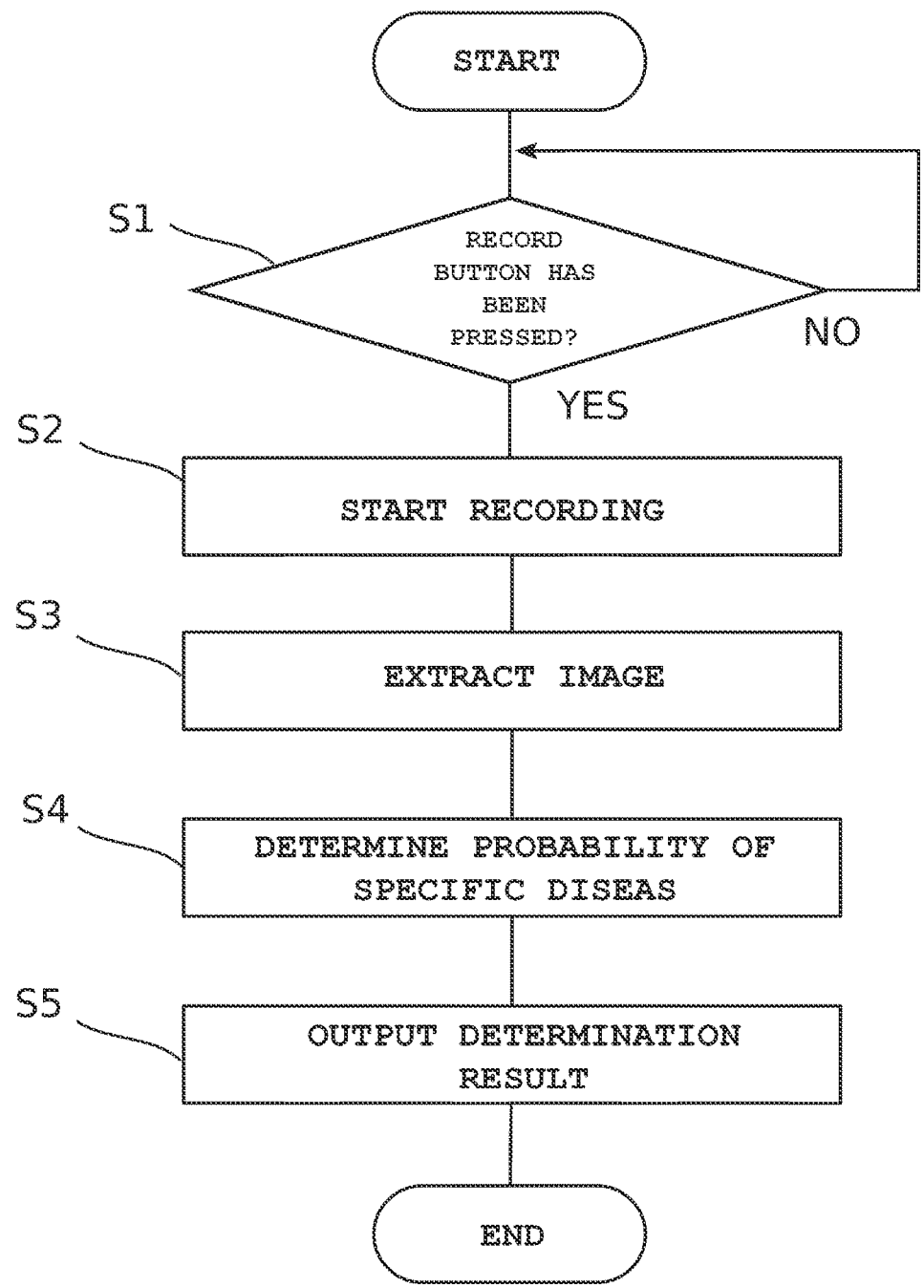
FIG. 20 is a flow chart for illustrating Operation Example 1 of the intraoral imaging apparatus (5) of FIG. 9.

Referring to FIG. 20, Operation Example 1 of the intraoral imaging apparatus 5 is described. Now, an operation performed when the intraoral imaging apparatus 5 captures a moving image is given as an example. However, the intraoral imaging apparatus 5 may capture a still image, and in this case as well, the intraoral imaging apparatus 5 operates in the same manner.

When the intraoral imaging apparatus 5 is powered on, the intraoral imaging apparatus 5 starts imaging by the imaging device 57 to display an image on the display, and determines in Step S1 whether or not a record button (one of the components of the input device 55) has been pressed. When the pressing of the record button is not confirmed, the intraoral imaging apparatus 5 repeats Step S1.

When the pressing of the record button is confirmed, the intraoral imaging apparatus 5 starts recording in Step S2. At the same time, the intraoral imaging apparatus 5 turns on the light source 58. The user attaches the intraoral imaging assistance tool 3 to the intraoral cavity 71 of the determination target person 7, and then inserts the imaging device 57 into the intraoral imaging assistance tool 3 (see FIG. 1). The imaging device 57 captures the image of the inside of the mouth (intraoral cavity 71 or pharynx 72) of the determination target person 7 even during the sliding in the intraoral imaging assistance tool 3.

In Step S3, the intraoral imaging apparatus 5 extracts an appropriate still image for determination from among a plurality of still images included in the acquired moving image. At this time, the extracted still image may be displayed on the display as an extraction result.

In Step S4, the intraoral imaging apparatus 5 determines a probability of a specific disease based on the extracted still image and the determination algorithm, and outputs a result of the determination to, for example, the display in Step S5. This brings the series of operations to an end.

In this manner, the possibility of the specific disease is evaluated through use of the determination algorithm generated by machine learning, and hence a highly accurate determination result can be expected.

An image with satisfactory imaging conditions is selected for determination, and hence accuracy of the determination is improved.

When the intraoral imaging apparatus 5 is used in combination with the intraoral imaging assistance tool 3, it is possible to obtain a clear image with a wide field of view. This contributes to improvement in determination accuracy.

3-5 Operation Example 2 of Intraoral Imaging Apparatus

Figure 21:
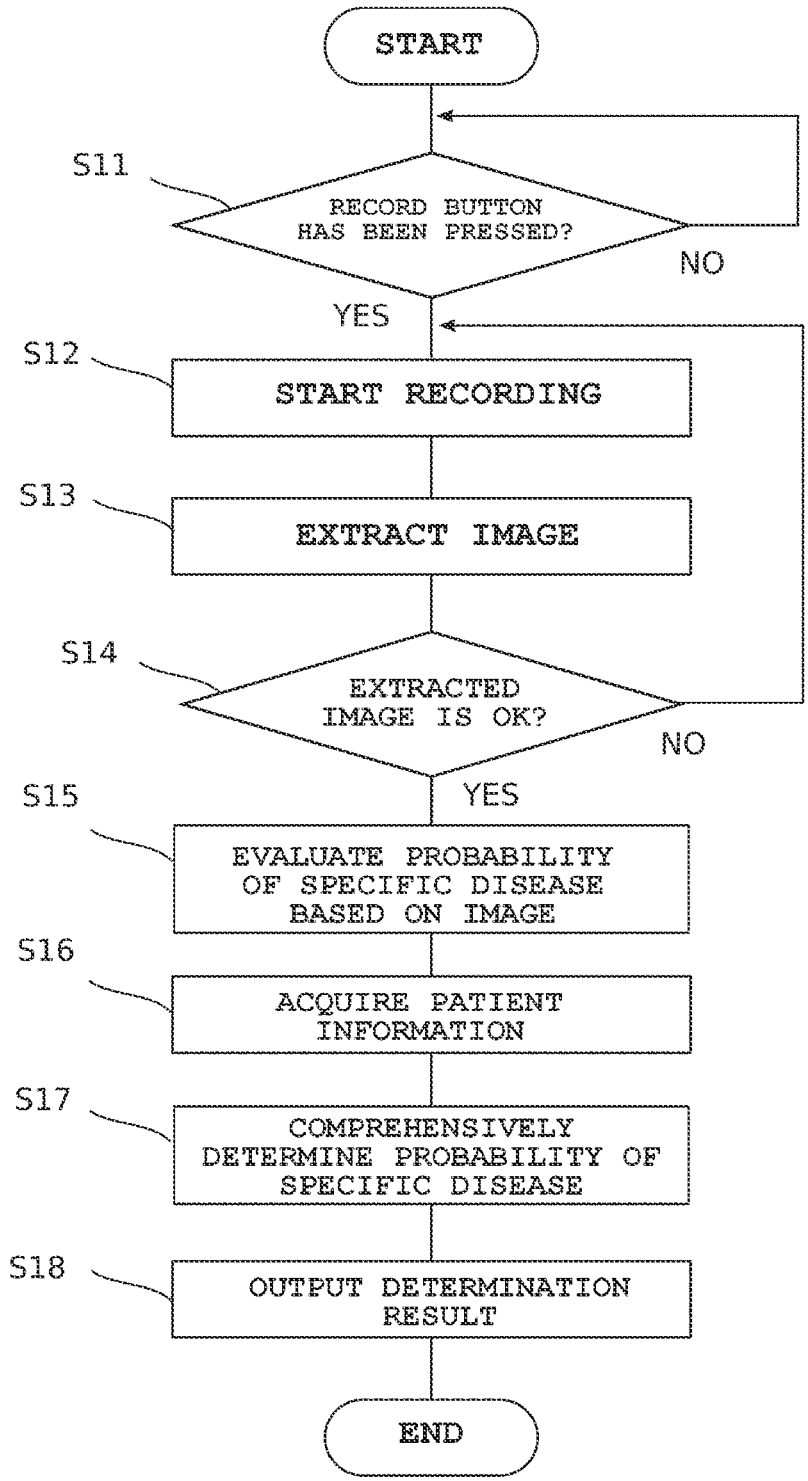
FIG. 21 is a flow chart for illustrating Operation Example 2 of the intraoral imaging apparatus (5) of FIG. 9.

Referring to FIG. 21, Operation Example 2 of the intraoral imaging apparatus 5 is described. Operation Example 2 includes the same types of steps as the above-mentioned steps of Operation Example 1, and further includes a step of verifying the extracted image by the user (Step S14), a patient information input step (Step S16), and comprehensive determination (Step S17).

Specifically, when the intraoral imaging apparatus 5 is powered on, the intraoral imaging apparatus 5 examines whether or not the record button has been pressed (Step S11), starts recording (Step S12), and extracts an image for the determination (Step S13). Then, the intraoral imaging apparatus 5 displays the extracted image on, for example, the display, and requests the user to verify whether or not to use the image for the determination (Step S14). When the user selects "NO," Step S12 and Step S13 are executed again to present a new image for the determination to the user.

When the user selects "YES" in Step S14, the intraoral imaging apparatus 5 determines the probability of the specific disease based on the extracted image (Step S15).

Subsequently, the intraoral imaging apparatus 5 requests the user to input the patient information (Step S16). In this case, the patient information is simple standardized information including a body temperature at a time of consultation and whether or not the patient is vaccinated. Such patient information is input in a form that can be uniformly processed by the software. For example, a pull-down menu or such an input form setting as to reject data other than half-width numbers may be used. In another case, the intraoral imaging apparatus 5 may acquire the patient information from an external computer (for example, electronic medical chart system) through a wired or wireless line. Step S16 may be executed prior to Step S11.

Then, both the above-mentioned patient information and the evaluation of the probability of the specific disease based on the image are integrated to calculate the probability of the disease as a whole (Step S17). A result of the calculation is displayed on, for example, the display (Step S18), and the series of procedural steps are ended.

In this manner, the intraoral imaging apparatus 5 evaluates the possibility of a specific disease based on the image verified by the user, to thereby improve the accuracy and reliability of the determination.

When the determination is further performed based on the patient information, it is expected that the accuracy and reliability of the determination are further improved.

3-6 Operation Example 3 of Intraoral Imaging Apparatus

Figure 24:
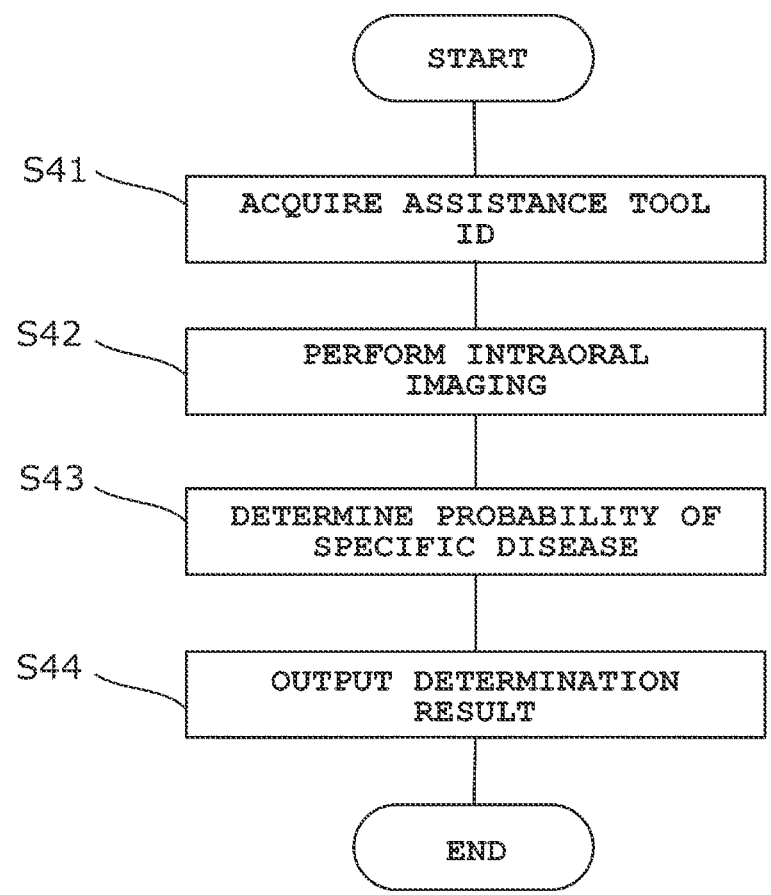
FIG. 24 is a flow chart for illustrating Operation Example 3 of the intraoral imaging apparatus (5) of FIG. 9.

Referring to FIG. 24, Operation Example 3 of the intraoral imaging apparatus 5 is described. Operation Example 3 includes a procedural step (Step S41) of acquiring the identification information on the intraoral imaging assistance tool 3.

Specifically, when the intraoral imaging apparatus 5 is powered on, in Step S41, the intraoral imaging apparatus 5 requests the user to input the identification information on the intraoral imaging assistance tool 3 through use of, for example, an indication on the display. For example, when the user captures the image of the identifier 91 on the pouch 9 by the imaging device 57 or inputs the identification information through use of the input device 55, the intraoral imaging apparatus 5 acquires the identification information on the intraoral imaging assistance tool 3.

The intraoral imaging apparatus 5 may examine the lot information on the intraoral imaging assistance tool 3 through use of the identification information. For example, the intraoral imaging apparatus 5 may search for whether or not the records in the ROM 53 include the product ID of the intraoral imaging assistance tool 3, or may cause an external computer to examine presence or absence of the product ID.

When the corresponding product ID is included in internal records or external records, the intraoral imaging apparatus 5 may output an alarm or end the series of processing steps. Examples of the alarm include an indication on the display that the intraoral imaging assistance tool 3 has been used. This limits the reuse of the intraoral imaging assistance tool 3 to enhance the safety of the intraoral imaging assistance tool 3 including the prevention of secondary infection. It is also possible to associate the intraoral imaging assistance tool 3 and the determination target person 7 for which the intraoral imaging assistance tool 3 has been used with each other on a one-to-one basis, to thereby facilitate a future follow-up survey.

After that, the intraoral imaging apparatus 5 performs intraoral imaging in Step S42. In this case, processing for capturing an image of the inside of the mouth may be the same as those described above in Operation Examples 1 and 2, or may be performed by a procedure described later. Then, the intraoral imaging apparatus 5 determines the probability of the specific disease in Step S43, outputs a result of the determination in Step S44, and ends the series of processing steps.

3-7 Another Example of Intraoral Imaging

Figure 25:
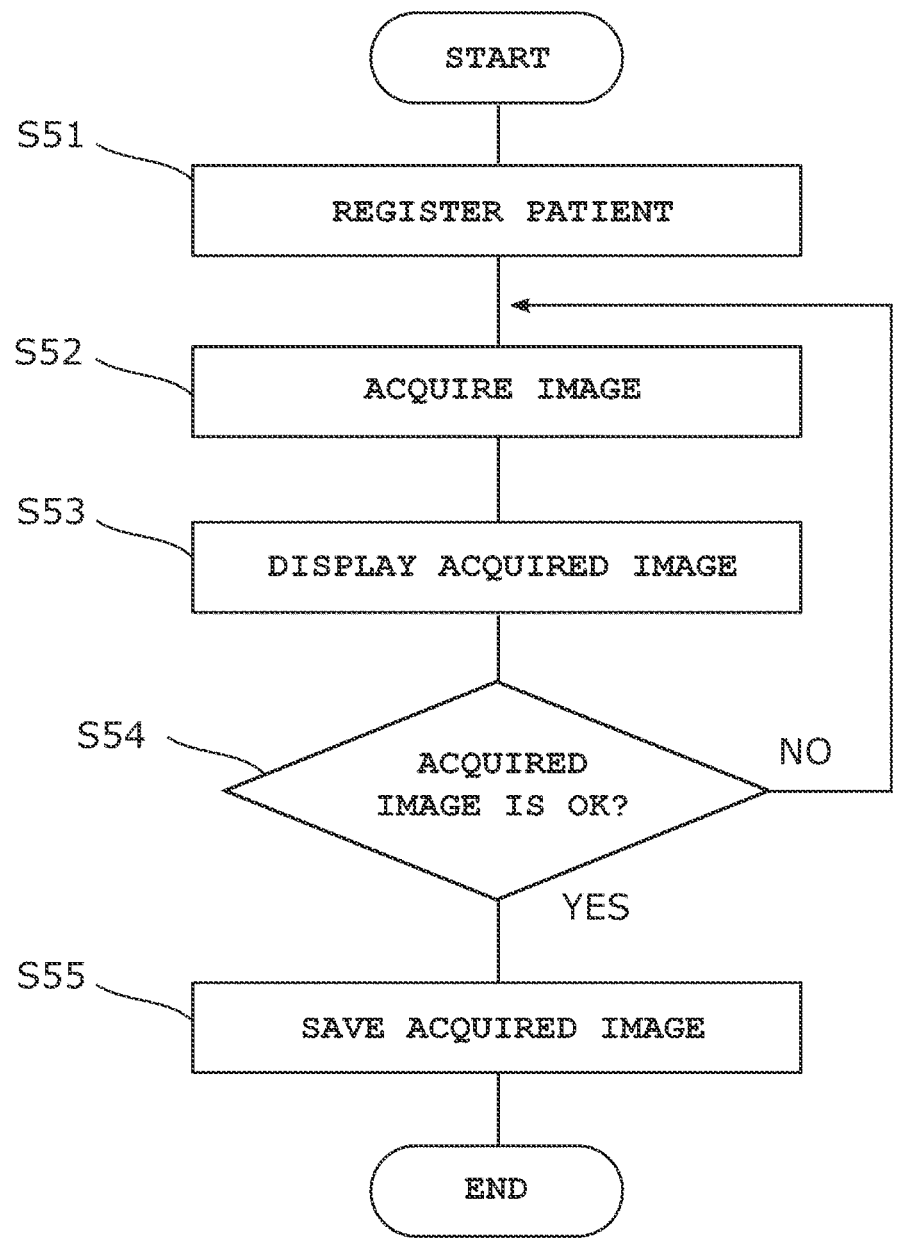
FIG. 25 is a flow chart for illustrating an example of an imaging operation of the intraoral imaging apparatus (5).

Referring to FIG. 25, another procedure for the intraoral imaging is described. The procedure described here can be replaced by the image acquisition procedures described above in Operation Examples 1 to 3. This procedure can also be used to collect training data for machine learning.

First, in Step S51, the intraoral imaging apparatus 5 registers a patient. The patient is registered by, for example, recording a patient ID captured or input by the user in the intraoral imaging apparatus 5.

Subsequently, in Step S52, the intraoral imaging apparatus 5 acquires an image. The image referred to here is a still image, and may be composed of, for example, a set of still images extracted from among images captured by the imaging device 57 at predetermined time intervals (for example, every second).

Then, in Step S53, the intraoral imaging apparatus 5 displays the acquired image on, for example, the display, and requests the user for verification. When approval is obtained from the user in Step S54, the intraoral imaging apparatus 5 saves the image approved in Step S55, and ends the series of processing steps for imaging. When the user's approval is not obtained, the process returns to Step S52 to acquire an image again.

Figure 26:
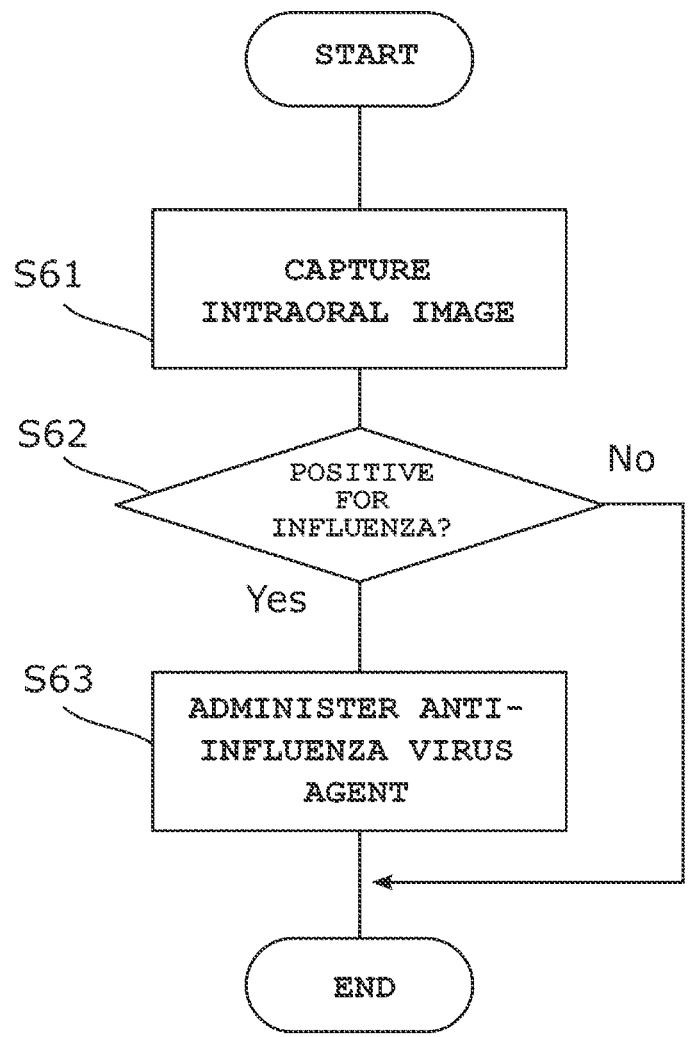
FIG. 26 is a flow chart for illustrating an example of a procedure from intraoral imaging to administration of an anti-influenza virus agent.

4 Procedure from Intraoral Imaging to Administration of Anti-Influenza Virus Agent Referring to FIG. 26, a procedure from the intraoral imaging to the administration of an anti-influenza virus agent is described.

In Step S61, the intraoral imaging apparatus 5 is used to capture an intraoral image, in particular, a pharyngeal image. At this time, in order to obtain a clear image, it is possible to use any one of the above-mentioned intraoral imaging assistance tools 3 (including those described in the modification examples).

Subsequently, in Step S62, it is determined whether the patient is positive or negative for an influenza virus infectious disease based on the intraoral image. For example, this step is preferred to include determining whether or not a pattern peculiar to the influenza virus infectious disease appears in the pharynx. This step can be executed through use of the intraoral imaging apparatus 5.

Then, when the determination result of Step S62 is negative for an influenza virus infectious disease, the series of procedural steps are ended.

In contrast, when the determination result is positive for an influenza virus infectious disease, in Step S63, the patient is administered an anti-influenza virus agent, and the series of procedural steps are ended. Thus, an anti-influenza virus agent can be promptly and accurately administered to the patient suspected of an influenza virus infectious disease, to thereby enable an efficient treatment of influenza. In addition, an anti-influenza virus agent is administered to patients who are positive for an influenza virus infectious disease, and thus it is possible to prevent an outbreak of a drug-resistant strain, which has become a social problem in Japan and around the world.

Herein, examples of the anti-influenza virus agent include baloxavir, oseltamivir, zanamivir, peramivir, and laninamivir. However, the anti-influenza virus agent is not limited to those small molecule drugs, and may be any other low-molecular-weight compound, peptide drug, antibody drug, nucleic acid drug, or vaccine having an antiviral action.

Examples of the small molecule drug having an antiviral action include: a compound having a Cap endonuclease-inhibiting action, such as baloxavir; a compound having a neuraminidase-inhibiting action, such as laninamivir, zanamivir, or a zanamivir analog AV-5080; a compound having an RNA polymerase-inhibiting action, such as favipiravir; a compound having a PB2 protein-inhibiting action, such as pimodivir or CC-42344; a compound having an antiviral action, such as nitazoxanide or tizoxanide (tizoxanid); and a compound having a G-protein-coupled receptor (GPCR) antagonistic action, such as GP-1001.

Examples of the peptide drug having an antiviral action include: flufirvitide-3, which targets influenza virus hemagglutinin HA2 and is formed of 16 amino acid residues; PD-001 (HA100, HA100-R14, iHA-100, iHA-24), which is a cyclic peptide targeting hemagglutinin (HA); a peptide (e.g., DAS-181) disclosed in U.S. Pat. No. 7,645,448 B2 and its family, which targets hemagglutinin (HA); TCN-032, which is a fully human monoclonal IgG antibody using the extracellular amino terminal region (M2e) of the matrix protein M2 of an influenza A virus as an antigen; and VIS-410, which a human IgG1 monoclonal antibody having a broad spectrum against influenza viruses and being capable of inhibiting the fusion of hemagglutinin (HA) and a cell membrane.

Examples of the antibody drug having an antiviral action include: gedivumab, which is a recombinant human monoclonal IgG1κ antibody against influenza A; MEDI-8852, which is an IgG1κ monoclonal antibody that binds to the stalk region of each of hemagglutinin (HA) subtypes H5 and H7; and CF-404, which is a mixture of three kinds of human monoclonal antibodies disclosed in WO 2014152841 A1 and its family, and targets a conserved region of influenza virus hemagglutinin (HA).

Examples of the nucleic acid having an antiviral action include: radavirsen, which is antisense RNA/DNA formed of 20 bases; and STP-702, which is an siRNA mixture targeting genes of influenza viruses 5N1, H1N1, and H7N9.

Examples of the influenza vaccine include: an inactivated whole virion nasal influenza vaccine (BK-1304) disclosed in WO 2014103488 A1 and its family; an intradermal administration-type influenza-preventing vaccine (DNK-651, KD-404); a nasal spray-type live attenuated quadrivalent vaccine (MEDI-3250/VN-0107/FluMist (trademark) Quadrivalent/Fluenz (trademark) Tetra); a sublingual tablet formulation of an influenza HA vaccine (NSV-0001); a pandemic influenza vaccine using recombinant hemagglutinin (HA) as an antigen, the vaccine being disclosed in WO 2014017493 A1 and its family and produced using transgenic *Bombyx mori*; a monovalent influenza VLP vaccine against influenza A; a nasal recombinant pandemic influenza vaccine targeting influenza hemagglutinin (HA) based on the use of a replication-deficient adenoviral vector; a nasal recombinant seasonal influenza vaccine targeting influenza hemagglutinin (HA) based on the use of a replication-deficient adenoviral vector; an H5N1 avian influenza vaccine (AE-443p) using a synthetic peptide; an alphavirus replicon vaccine (AVX-502) expressing an influenza HA protein; a DNA vaccine (pH7HA/GLS-3700) synthesized by incorporating a hemagglutination (HA) influenza antigen gene derived from a patient infected with influenza H7N9 into a pGX0001 expression vector; an AS03-adjuvanted inactivated trivalent influenza vaccine (GSK-2186877A); an H7N9 influenza vaccine (GSK-3206641A) containing an AS03 adjuvant and using influenza virus hemagglutinin protein (HA) as an antigen; a DNA vaccine (pH3HA) against an H3N2 influenza virus; a DNA vaccine (INO-3510) that contains an influenza A H5N1 vaccine (INO-3401) and H1N1 vaccines (INO-3605 and INO-3609), and is intradermally administered through use of electroporation; a RedeeFlu™ vaccine (Bris10 M2SR) formed of an influenza virus with a partial deletion of the M2 gene; a vaccine (MER-4101) obtained by formulating three kinds of standard seasonal inactivated influenza antigens into a nanoparticle W/O emulsion formulation with MAS-1 (Mercia Adjuvant/delivery System-1) from Mercia Pharma Inc.; a vaccine (mRNA-1851) using mRNA encoding a membrane-bound hemagglutinin protein H7; a vaccine (MT-8972) that is disclosed in WO 2009009876 A1 and its family and targets an Indonesia influenza A virus (A/Indonesia/5/2005); an H5 influenza vaccine (nanoemulsion adjuvanted H5 influenza vaccine) that contains a plant-derived influenza (influenza A/Indonesia/5/2005) HA antigen (H5) and induces an anti-H5 antibody; a vaccine (PDS-0103) obtained by encapsulating an influenza antigen in a nanoparticle formed of a cationic lipid (DOTAP); a quadrivalent influenza vaccine (MT-2271) targeting 1N1 (A/California/04/09), H3N2 (A/Victoria361/2011), and two kinds of type B strains (B/Wisconsin/1/2010, B/Brisbane/60/2008), the vaccine utilizing *Nicotiana benthamiana* in the production of its virus-like particle (VLP); an H5N1 influenza vaccine (PXVX-0103) obtained by incorporating the H5 HA antigen of an H5N1 influenza virus (A/Vietnam/1194/2004) into an adenoviral vector (Ad4), the vaccine being replicated in the small intestine to induce an antibody reaction; a quadrivalent vaccine against seasonal influenza including type B influenza produced using the core virus-like particle (VLP) technology of Novavax; a quadrivalent oral vaccine against seasonal influenza, wherein an adenovirus (Ad5) containing dsRNA encoding an HA antigen and a TLR3 ligand is absorbed through the small intestine, and the TLR3 ligand activates dendritic cells and induces antibody production; and a preventive DNA vaccine (VGX-3400X) against H5N1 and H7N9 avian influenza viruses, the vaccine being formed of three kinds of DNA plasmids respectively containing a universal consensus hemagglutinin (HA) derived from a plurality of different H5N1 viruses, a universal consensus neuraminidase (NA) encompassing N1 subtypes, such as H5N1 and H1N1, and a universal consensus nucleoprotein (NP) fused to a portion of the m2 protein (m2e).

In Step S63, the anti-influenza virus agent may also be administered to a close contact of the patient determined to be positive for the influenza virus infectious disease. In this case, a close contact of a patient suspected of being infected with an influenza virus can be prevented from being infected with the influenza virus, and hence the spread of the influenza virus infectious disease can be effectively suppressed. Particularly in the case where the close contact is an elderly person aged 65 or more, a patient with a chronic respiratory disease or a chronic heart disease, a patient with a metabolic disease including diabetes, or a patient with renal dysfunction, who may become a high-risk patient when infected with the influenza virus infectious disease, a great preventive effect can be expected. The term "close contact" as used herein refers to, for example, a person who has acted with a patient determined to be suspected of the influenza virus infectious disease, has touched the patient, or has sat in a seat near the patient in an aircraft, a workplace, or the like, and the term encompasses family members living together and people living together.

A typical embodiment of the present invention has been described above, but the present invention is not limited thereto. Various design modifications may be made, and such modifications are also included in the present invention.

For example, the present invention may be understood as a treatment method and prevention method for an influenza virus infectious disease, and a therapeutic agent and preventive agent therefor, each containing an anti-influenza virus agent as an active ingredient.

As the treatment method, the present invention more specifically relates to a treatment method for an influenza virus infectious disease, containing an anti-influenza virus agent as an active ingredient, the treatment method including:

(1) performing diagnostic imaging for an influenza virus infectious disease through use of an intraoral imaging apparatus in the mouth of a patient suspected of the influenza virus infectious disease, followed by identifying and selecting a patient determined to be positive for the influenza virus infectious disease; and (2) administering the anti-influenza virus agent to the patient determined to be positive for the influenza virus infectious disease.

In addition, as the therapeutic agent, the present invention may relate to a therapeutic agent for an influenza virus infectious disease, containing an anti-influenza virus agent as an active ingredient, wherein the anti-influenza virus agent is administered to a patient determined to be positive for the influenza virus infectious disease based on an intraoral image captured using an intraoral imaging apparatus.

Alternatively, the present invention may be understood as a use of an active ingredient for manufacturing an anti-influenza virus agent for treating and preventing an influenza virus infectious disease. More specifically, the present invention relates to a use of an active ingredient for manufacturing an anti-influenza virus agent for treating an influenza virus infectious disease, wherein:

(1) diagnostic imaging for an influenza virus infectious disease is performed through use of an intraoral imaging apparatus in the mouth of a patient suspected of the influenza virus infectious disease, followed by identification and selection of a patient determined to be positive for the influenza virus infectious disease; and (2) the anti-influenza virus agent is administered to the patient determined to be positive for the influenza virus infectious disease.

In this embodiment, the anti-influenza virus agent is administered to the patient determined to be positive for the influenza virus infectious disease and the close contact thereof. However, the anti-influenza virus agent may also be administered to a subject determined to be negative for the influenza virus infectious disease (person determined negative) when close contacts thereof include a person who has developed the influenza virus infectious disease. In this case, a person at a risk of being infected with an influenza virus can be prevented from being infected with the influenza virus, and hence the spread of the influenza virus infectious disease can be effectively suppressed. Particularly in the case where the person determined negative is an elderly person aged 65 or more, a patient with a chronic respiratory disease or a chronic heart disease, a patient with a metabolic disease including diabetes, or a patient with renal dysfunction, a great preventive effect can be expected.

The invention claimed is:

1. A pharmaceutical composition for treating an influenza virus infectious disease, comprising an anti-influenza virus agent as an active ingredient,
wherein the anti-influenza virus agent is administered to a patient determined to be positive for the influenza virus infectious disease based on an intraoral image captured using an intraoral imaging apparatus.

2. The pharmaceutical composition for treating an influenza virus infectious disease according to claim 1,
wherein the intraoral imaging apparatus includes:
an imaging device configured to acquire the intraoral image of an inside of a mouth; and
a light source configured to emit light to a subject of the imaging device,
a possible presence of the influenza virus infectious disease is determined based on the intraoral image and an algorithm stored in a memory, and
a determination result of the possible presence of the influenza virus infectious disease is output via an output device.

3. The pharmaceutical composition for treating an influenza virus infectious disease according to claim 2,
wherein the imaging device is configured to acquire the intraoral image of a pharynx, and
wherein the possible presence of the influenza virus infectious disease is determined under a condition in which whether a pattern peculiar to the influenza virus infectious disease appears in the pharynx of the intraoral image.

4. The pharmaceutical composition for treating an influenza virus infectious disease according to claim 1,
wherein the anti-influenza virus agent is selected from the group consisting of: baloxavir; oseltamivir; zanamivir; peramivir; and laninamivir.

5. A pharmaceutical composition for preventing an influenza virus infectious disease, comprising an anti-influenza virus agent as an active ingredient,
wherein the anti-influenza virus agent is administered to a close contact of a patient determined to be positive for the influenza virus infectious disease based on an intraoral image captured using an intraoral imaging apparatus.

6. The pharmaceutical composition for preventing an influenza virus infectious disease according to claim 5,
wherein the close contact is an elderly person aged 65 or more, a patient with a chronic respiratory disease or a chronic heart disease, a patient with a metabolic disease including diabetes, or a patient with renal dysfunction.

7. The pharmaceutical composition for preventing an influenza virus infectious disease according to claim 5,
wherein the intraoral imaging apparatus includes:
an imaging device configured to acquire the intraoral image of an inside of a mouth; and
a light source configured to emit light to a subject of the imaging device,
a possible presence of the influenza virus infectious disease is determined based on the intraoral image and an algorithm stored in a memory, and
a determination result of the possible presence of the influenza virus infectious disease is output via an output device.

8. The pharmaceutical composition for preventing an influenza virus infectious disease according to claim 7,
wherein the imaging device is configured to acquire the intraoral image of a pharynx, and
wherein the possible presence of the influenza virus infectious disease is determined under a condition in which whether a pattern peculiar to the influenza virus infectious disease appears in the pharynx of the intraoral image.

9. A pharmaceutical composition for preventing an influenza virus infectious disease, comprising an anti-influenza virus agent as an active ingredient,
wherein the anti-influenza virus agent is administered to a person determined to be negative for the influenza virus infectious disease based on an intraoral image captured using an intraoral imaging apparatus, and the person, who is determined to be negative for the influenza virus infectious disease, has a close contact who has developed the influenza virus infectious disease.

10. The pharmaceutical composition for preventing an influenza virus infectious disease according to claim 9,
wherein the person is an elderly person aged 65 or more, a patient with a chronic respiratory disease or a chronic heart disease, a patient with a metabolic disease including diabetes, or a patient with renal dysfunction.

11. The pharmaceutical composition for preventing an influenza virus infectious disease according to claim 9,
wherein the intraoral imaging apparatus includes:
an imaging device configured to acquire the intraoral image of an inside of a mouth; and
a light source configured to emit light to a subject of the imaging device,
a possible presence of the influenza virus infectious disease is determined based on the intraoral image and an algorithm stored in a memory, and
a determination result of the possible presence of the influenza virus infectious disease is output via an output device.

12. The pharmaceutical composition for preventing an influenza virus infectious disease according to claim 11,
wherein the imaging device is configured to acquire the intraoral image of a pharynx, and
wherein the possible presence of the influenza virus infectious disease is determined under a condition in which whether a pattern peculiar to the influenza virus infectious disease appears in the pharynx of the intraoral image.

13. The pharmaceutical composition for treating an influenza virus infectious disease according to claim 2,
wherein the anti-influenza virus agent is selected from the group consisting of: baloxavir; oseltamivir; zanamivir; peramivir; and laninamivir.

14. The pharmaceutical composition for treating an influenza virus infectious disease according to claim 3,
wherein the anti-influenza virus agent is selected from the group consisting of: baloxavir; oseltamivir; zanamivir; peramivir; and laninamivir.

15. The pharmaceutical composition for preventing an influenza virus infectious disease according to claim 6,
wherein the intraoral imaging apparatus includes:
an imaging device configured to acquire the intraoral image of an inside of a mouth; and a light source configured to emit light to a subject of the imaging device, a possible presence of the influenza virus infectious disease is determined based on the intraoral image and an algorithm stored in a memory, and a determination result of the possible presence of the influenza virus infectious disease is output via an output device.

16. The pharmaceutical composition for preventing an influenza virus infectious disease according to claim 15, wherein the imaging device is configured to acquire the intraoral image of a pharynx, and wherein the possible presence of the influenza virus infectious disease is determined under a condition in which whether a pattern peculiar to the influenza virus infectious disease appears in the pharynx of the intraoral image.

17. The pharmaceutical composition for preventing an influenza virus infectious disease according to claim 10, wherein the intraoral imaging apparatus includes:

an imaging device configured to acquire the intraoral image of an inside of a mouth; and a light source configured to emit light to a subject of the imaging device, a possible presence of the influenza virus infectious disease is determined based on the intraoral image and an algorithm stored in a memory, and a determination result of the possible presence of the influenza virus infectious disease is output via an output device.

18. The pharmaceutical composition for preventing an influenza virus infectious disease according to claim 17, wherein the imaging device is configured to acquire the intraoral image of a pharynx, and wherein the possible presence of the influenza virus infectious disease is determined under a condition in which whether a pattern peculiar to the influenza virus infectious disease appears in the pharynx of the intraoral image.

\* \* \* \* \*